(12) United States Patent
Perry et al.

(10) Patent No.: US 9,351,976 B2
(45) Date of Patent: May 31, 2016

(54) PHARMACEUTICAL COMPOSITIONS COMPRISING SORBITAN ESTERS

(71) Applicant: Alkermes Pharma Ireland Limited, Dublin (IE)

(72) Inventors: Jason M. Perry, Cambridge, MA (US); Daniel R. Deaver, Franklin, MA (US); Magali B. Hickey, Westwood, MA (US); Julius F. Remenar, Framingham, MA (US); Jennifer Vandiver, Arlington, MA (US)

(73) Assignee: ALKERMES PHARMA IRELAND LIMITED, Dublin (IE)

( * ) Notice: Subject to any disclaimer, the term of this patent is extended or adjusted under 35 U.S.C. 154(b) by 0 days.

(21) Appl. No.: 14/714,621

(22) Filed: May 18, 2015

(65) Prior Publication Data

US 2015/0258115 A1    Sep. 17, 2015

Related U.S. Application Data

(62) Division of application No. 13/423,606, filed on Mar. 19, 2012, now Pat. No. 9,034,867.

(60) Provisional application No. 61/454,008, filed on Mar. 18, 2011.

(51) Int. Cl.
| | |
|---|---|
| *A61K 31/551* | (2006.01) |
| *A61K 9/00* | (2006.01) |
| *A61K 47/26* | (2006.01) |
| *A61K 31/5513* | (2006.01) |
| *A61K 31/4965* | (2006.01) |
| *A61K 31/497* | (2006.01) |
| *A61K 9/10* | (2006.01) |
| *A61K 31/496* | (2006.01) |

(52) U.S. Cl.
CPC .......... *A61K 31/5513* (2013.01); *A61K 9/0019* (2013.01); *A61K 9/10* (2013.01); *A61K 31/496* (2013.01); *A61K 31/497* (2013.01); *A61K 31/4965* (2013.01); *A61K 31/551* (2013.01); *A61K 47/26* (2013.01)

(58) Field of Classification Search
CPC ............ A61K 9/0019; A61K 31/4965; A61K 31/497; A61K 31/496; A61K 31/5513; A61K 47/26; A61K 9/10; A61K 31/551
See application file for complete search history.

(56) References Cited

U.S. PATENT DOCUMENTS

| | | |
|---|---|---|
| 2,418,499 A | 4/1947 | Burke |
| 3,266,984 A | 8/1966 | Sadao Horie et al. |
| 3,523,121 A | 8/1970 | Lewis et al. |
| 3,573,308 A | 3/1971 | Ning et al. |
| 3,957,808 A | 5/1976 | Miller et al. |
| 4,160,099 A | 7/1979 | Bodor |
| 4,204,065 A | 5/1980 | Bodor |
| 4,260,769 A | 4/1981 | Stella et al. |
| 4,428,935 A | 1/1984 | Myers |
| 4,443,464 A | 4/1984 | Biedermann et al. |
| 4,594,190 A | 6/1986 | Giani et al. |
| 4,694,006 A | 9/1987 | Bundgaard et al. |
| 4,727,151 A | 2/1988 | Bodor |
| 4,760,057 A | 7/1988 | Alexander |
| 4,837,337 A | 6/1989 | Murao et al. |
| 4,914,094 A | 4/1990 | Oshiro et al. |
| 4,992,550 A | 2/1991 | Hughes |
| 5,006,528 A | 4/1991 | Oshiro et al. |
| 5,206,386 A | 4/1993 | Narayanan et al. |
| 5,236,927 A | 8/1993 | Jones et al. |
| 5,350,747 A | 9/1994 | Howard |
| 5,462,934 A | 10/1995 | Goto et al. |
| 5,700,946 A | 12/1997 | Shimasaki et al. |
| 5,719,303 A | 2/1998 | Yoshida et al. |
| 5,783,589 A | 7/1998 | Latimer et al. |
| 5,985,856 A | 11/1999 | Stella et al. |
| 6,127,357 A | 10/2000 | Cliffe et al. |
| 6,133,248 A | 10/2000 | Stella |
| 6,180,095 B1 | 1/2001 | Greenwald et al. |
| 6,608,084 B1 | 8/2003 | Bourzat et al. |
| 6,653,312 B1 | 11/2003 | Auvin et al. |
| 6,656,932 B2 | 12/2003 | Picard et al. |
| 6,977,257 B2 | 12/2005 | Parab et al. |
| 7,053,092 B2 | 5/2006 | Jordon et al. |
| 7,112,603 B2 | 9/2006 | Moon et al. |
| 7,115,587 B2 | 10/2006 | Nerurkar et al. |
| 7,160,888 B2 | 1/2007 | Johnson et al. |

(Continued)

FOREIGN PATENT DOCUMENTS

| | | |
|---|---|---|
| EP | 1891956 A1 | 12/2008 |
| GB | 849541 A1 | 9/1960 |
| GB | 2017701 A | 10/1979 |
| WO | 9014080 A1 | 11/1990 |
| WO | 9100863 A1 | 1/1991 |
| WO | 9325197 A1 | 12/1993 |
| WO | 9612725 A1 | 5/1996 |
| WO | 9743284 A1 | 11/1997 |
| WO | 9933846 A2 | 7/1999 |
| WO | 02096351 A2 | 12/2002 |
| WO | 2004026864 A1 | 4/2004 |

(Continued)

OTHER PUBLICATIONS

Shintani, et al: A new method to determine the irritation of drugs after intramuscular injection in rabbits; Toxicology and Applied Pharmacology; Academic Press, U.S., Sep. 1, 1967; Vo. 11, No. 2, pp. 293-295.

(Continued)

*Primary Examiner* — Johann R Richter
*Assistant Examiner* — Genevieve S Alley
(74) *Attorney, Agent, or Firm* — Lathrop & Gage LLP; Brian C. Trinque; Benjamin D. Heuberger

(57) ABSTRACT

The present invention relates to a pharmaceutical composition comprising sorbitan esters of carboxylic acids that are useful for the delivery of anti-psychotic drugs.

20 Claims, 9 Drawing Sheets

(56) References Cited

U.S. PATENT DOCUMENTS

| | | |
|---|---|---|
| 7,538,121 B2 | 5/2009 | MacDonald et al. |
| 7,550,445 B2 | 6/2009 | Nerurkar et al. |
| 7,807,680 B2 | 10/2010 | Kostanski et al. |
| 8,017,615 B2 | 9/2011 | Bando et al. |
| 8,030,313 B2 | 10/2011 | Kostanski et al. |
| 8,338,427 B2 | 12/2012 | Brown |
| 8,338,428 B2 | 12/2012 | Brown |
| 8,399,469 B2 | 3/2013 | Bando et al. |
| 8,431,576 B2 | 4/2013 | Remenar et al. |
| 8,518,421 B2 | 8/2013 | Kothari et al. |
| 8,536,328 B2 | 9/2013 | Remenar et al. |
| 8,580,796 B2 | 11/2013 | Bando et al. |
| 8,642,600 B2 | 2/2014 | Jordan et al. |
| 8,642,760 B2 | 2/2014 | Bando et al. |
| 2002/0176841 A1 | 11/2002 | Barker et al. |
| 2005/0019436 A1 | 1/2005 | Burch et al. |
| 2005/0032811 A1 | 2/2005 | Brown |
| 2005/0203089 A1 | 9/2005 | Starrett, Jr. et al. |
| 2005/0282821 A1 | 12/2005 | Lesur et al. |
| 2006/0142333 A1 | 6/2006 | MacDonald et al. |
| 2006/0293217 A1 | 12/2006 | Barker et al. |
| 2007/0031513 A1 | 2/2007 | Kikuchi et al. |
| 2007/0191611 A1 | 8/2007 | Rao et al. |
| 2008/0085888 A1 | 4/2008 | Breining et al. |
| 2008/0186971 A1 | 8/2008 | Carmichael et al. |
| 2008/0261954 A1 | 10/2008 | Maelicke |
| 2008/0312199 A1 | 12/2008 | Glinsky |
| 2008/0318905 A1 | 12/2008 | Muhammad et al. |
| 2009/0053329 A1 | 2/2009 | Peters et al. |
| 2009/0068290 A1 | 3/2009 | Bourin et al. |
| 2009/0118242 A1* | 5/2009 | Burch et al. .................. 514/162 |
| 2009/0143403 A1 | 6/2009 | Brown |
| 2009/0163519 A1 | 6/2009 | Vermeulen et al. |
| 2009/0163545 A1 | 6/2009 | Goldfarb |
| 2010/0286136 A1 | 11/2010 | Jones et al. |
| 2010/0292316 A1 | 11/2010 | Sanders et al. |
| 2011/0003828 A1 | 1/2011 | Blumberg et al. |
| 2011/0015156 A1 | 1/2011 | Remenar et al. |
| 2011/0166128 A1* | 7/2011 | Remenar et al. ............. 514/220 |
| 2011/0166156 A1 | 7/2011 | Blumberg et al. |
| 2011/0166194 A1 | 7/2011 | Blumberg et al. |
| 2011/0178068 A1 | 7/2011 | Almarsson et al. |
| 2011/0236478 A1 | 9/2011 | Dokou et al. |
| 2011/0275803 A1 | 11/2011 | Remenar et al. |
| 2011/0319422 A1 | 12/2011 | Blumberg et al. |
| 2012/0015866 A1 | 1/2012 | Blumberg et al. |
| 2012/0238552 A1 | 9/2012 | Perry et al. |
| 2013/0096089 A1 | 4/2013 | Remenar et al. |
| 2013/0267505 A1 | 10/2013 | Perry et al. |

FOREIGN PATENT DOCUMENTS

| | | |
|---|---|---|
| WO | 2004067546 A1 | 8/2004 |
| WO | 2004089925 A1 | 10/2004 |
| WO | 2005016262 A2 | 2/2005 |
| WO | 2005066165 A1 | 7/2005 |
| WO | 2005079807 A1 | 9/2005 |
| WO | 2006037090 A2 | 4/2006 |
| WO | 2006055603 A2 | 5/2006 |
| WO | 2006090273 A2 | 8/2006 |
| WO | 2007059111 A2 | 5/2007 |
| WO | 2009052467 A1 | 4/2009 |
| WO | 2010151689 A1 | 12/2010 |
| WO | 2010151711 A1 | 12/2010 |
| WO | 2011084848 A2 | 7/2011 |
| WO | 2012129156 A1 | 9/2012 |

OTHER PUBLICATIONS

International Search Report, PCT/US2012/029625, dated Aug. 28, 2012, 8 pages.

International Preliminary Report on Patentability, PCT/US2012/029625, dated Sep. 24, 2013, 11 pages.

Dai et al., (2007) "Parallel screening approach to identify solubility-enhancing formulations for improved bioavailability of a poorly water-soluble compound using milligram quantities of material" International Journal of Pharmaceutics, 336, 1-11.

Porras et al., (2004) "Studies of formation of W/O nano-emulsions" Colloids and Surfaces A: Physicochem. Eng. Aspects, 249, 115-118.

Shinde et al., (2011) "Microemulsions and Nanoemulsions for Targeted Drug Delivery to the Brain" Current Nanoscience, 7, 119-133.

* cited by examiner

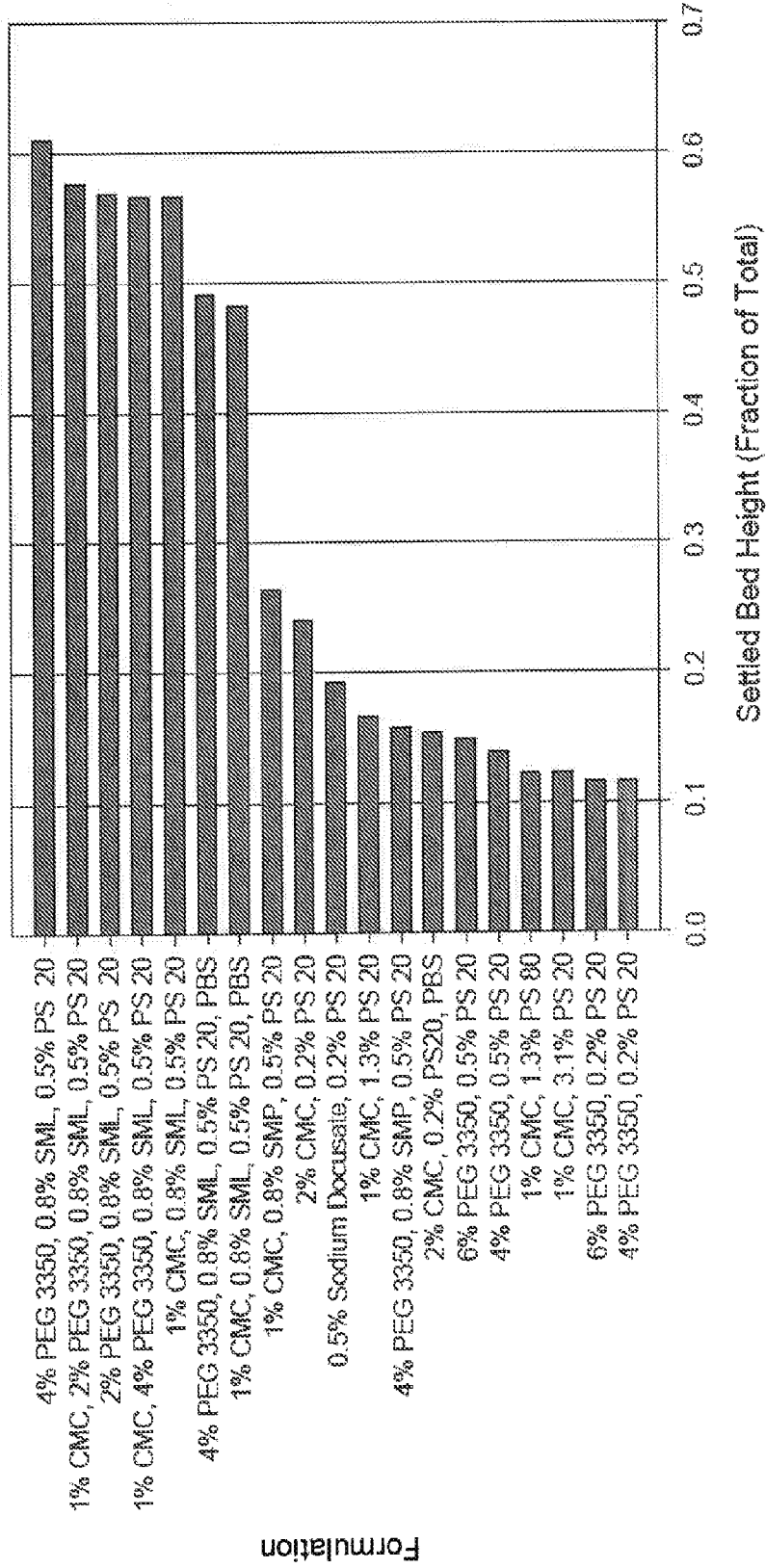

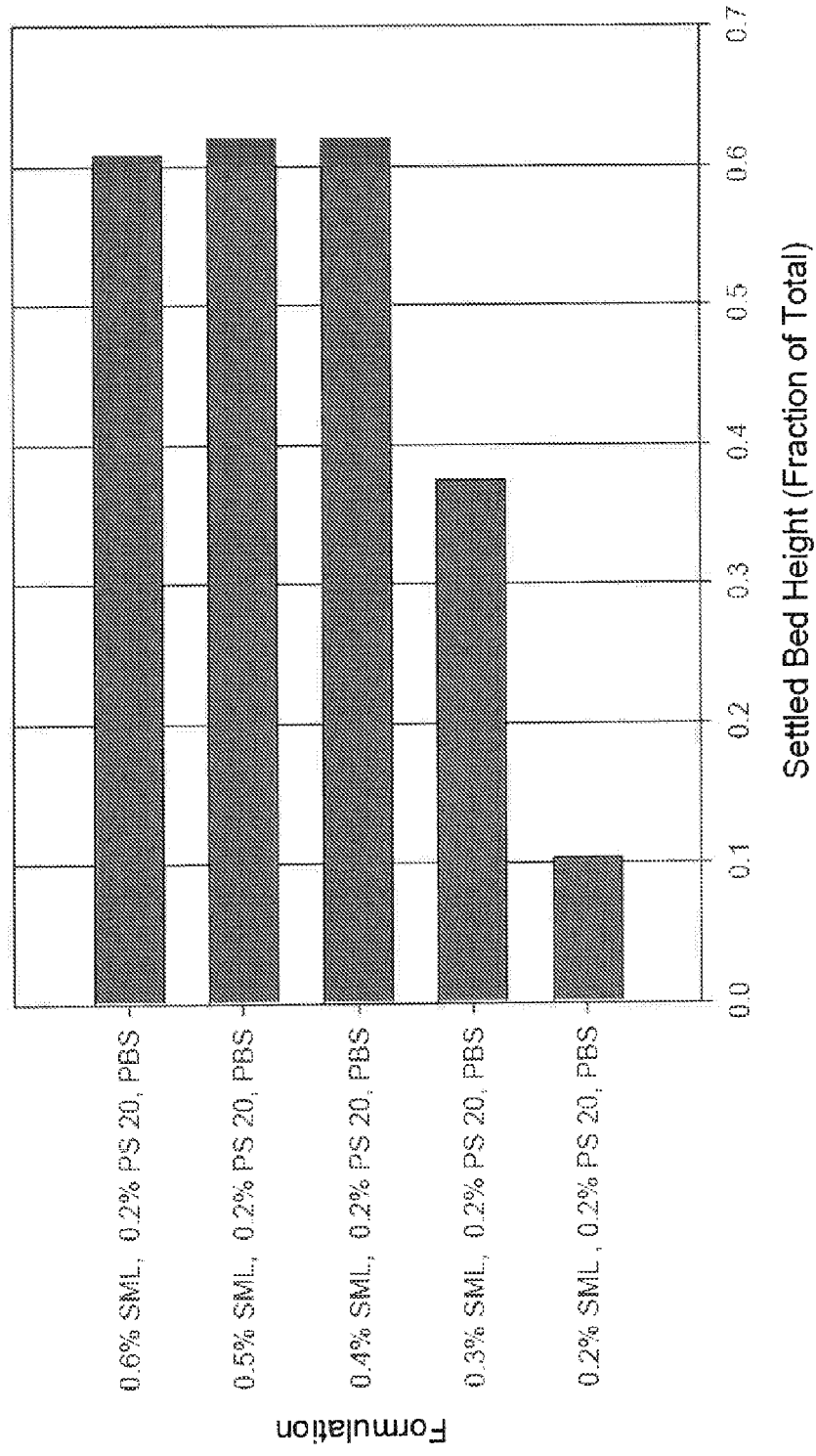

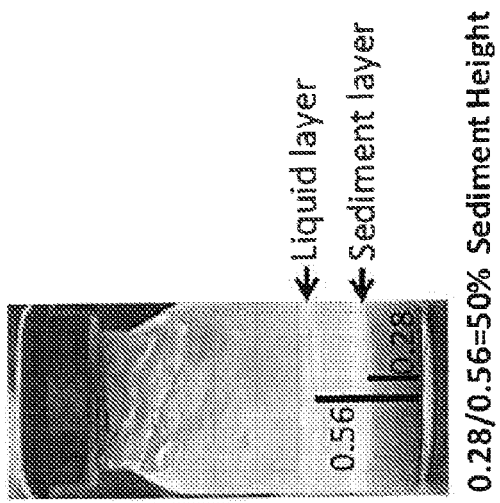
Figure 3: Example photograph illustrating the sediment height measurement on a vial

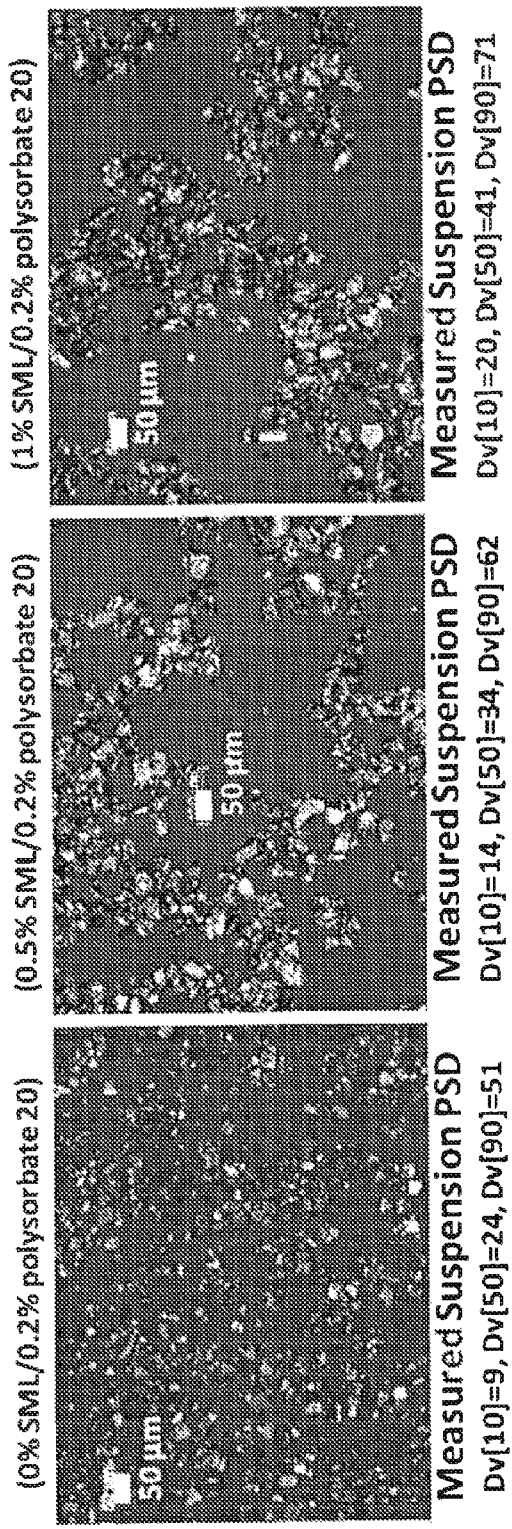
Figure 4: Microscopy of three suspensions made with vehicle containing 0.2% polysorbate 20 and increasing amounts of SML from 0% (far left) to 1% SML (far right)

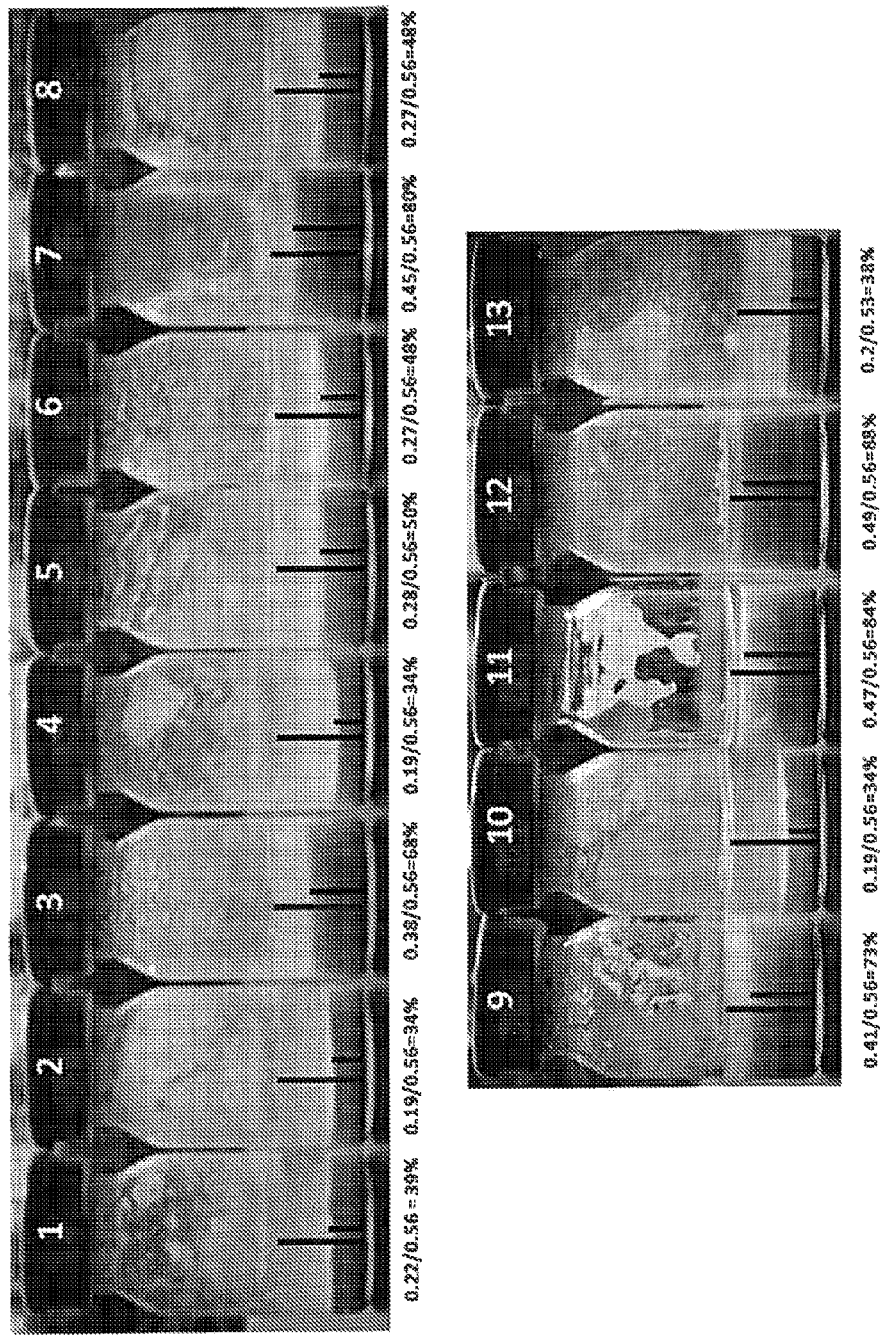
Figure 5: Sediment height calculations for vials containing Compond A-7 suspensions having varying SML and polysorbate 20 concentrations

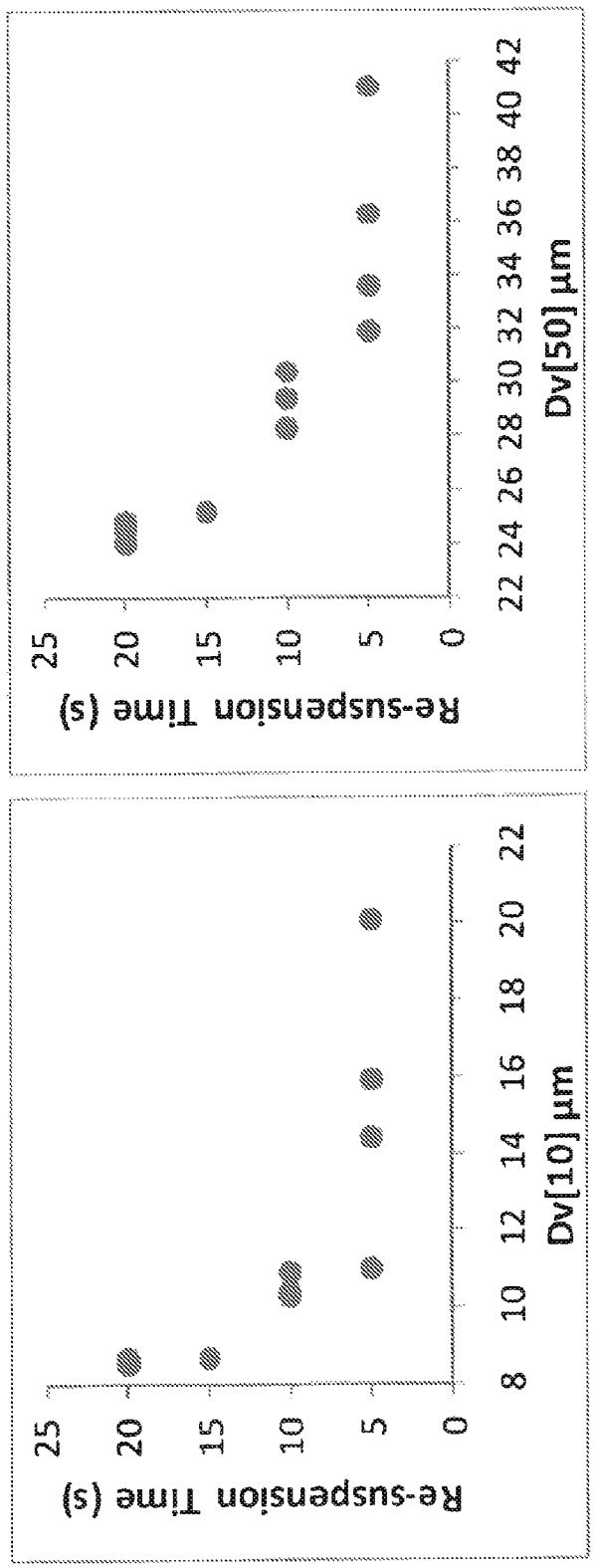
Figure 6: Plots of re-suspension time as a function of Dv[10] (left) and Dv[50] (right) in microns

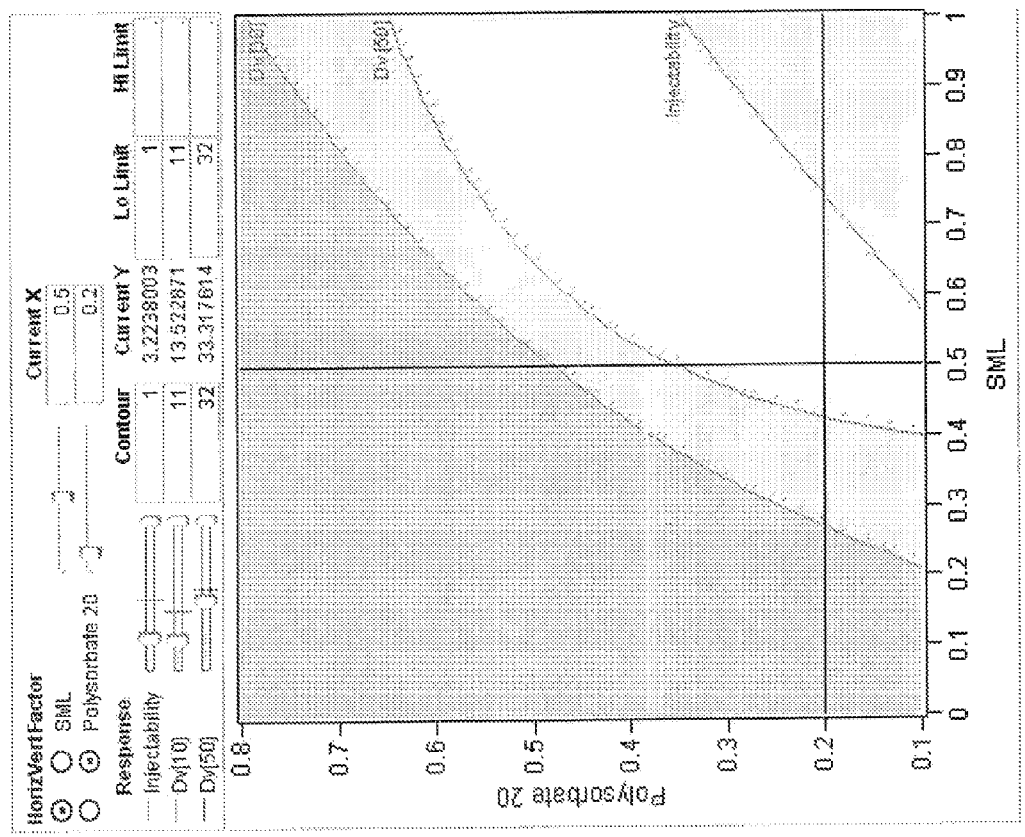
Figure 7: Contour plot of formulation space including limits

PHARMACEUTICAL COMPOSITIONS COMPRISING SORBITAN ESTERS

RELATED APPLICATION

This application is a divisional of U.S. patent application Ser. No. 13/423,606, filed Mar. 19, 2012, which claims priority to U.S. Provisional Application No. 61/454,008, titled "Formulations Having Improved Site Reactions", filed on Mar. 18, 2011. The contents of any patents, patent applications, and references cited throughout this specification are hereby incorporated by reference in their entireties.

TECHNICAL FIELD

The present invention relates to an injectable, pharmaceutical composition comprising sorbitan esters of carboxylic acids that are useful for the delivery of anti-psychotic drugs.

BACKGROUND OF THE INVENTION

U.S. Pat. Nos. 4,734,416 and 5,006,528 discloses aripiprazole, 7-{4-[4-(2,3-dichlorophenyl)-1-piperazinyl]butoxy}-3,4-dihydro-2(1H)-quinolinone or 7-{4-[4-(2,3-dichlorophenyl)-1-piperazinyl]butoxy}-3,4-dihydro carbostyril, as an atypical antipsychotic agent useful in the treatment of schizophrenia, bipolar disease, depression and other CNS disorders. Aripiprazole has the following chemical structure:

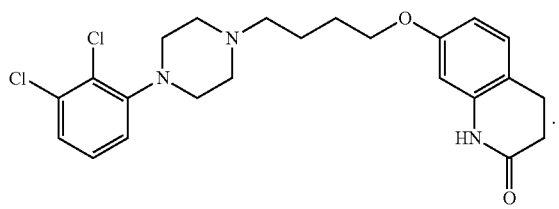 [SMILES: O=C1CCc2ccc(OCCCCN3CCN(c4cccc(Cl)c4Cl)CC3)cc2N1]

Aripiprazole is sold under the tradename Ability®. It acts as a dopamine $D_2$ partial agonist, serotonin 5-$HT_{1A}$ receptor agonist and is an antagonist of the serotonin 5-$HT_{2A}$ receptor. Abilify® is currently administered orally on a once-a-day dosing schedule as Abilify® (aripiprazole) Tablets, Ability Discmelt® (aripiprazole) Orally Disintegrating Tablets and Abilify® (aripiprazole) Oral Solution. In one embodiment, Abilify® Injection for intramuscular use is a rapid-acting solution product for treating agitation associated with schizophrenia and bipolar disease. Poor and variable patient compliance with a once-a-day dosing schedule of psychiatric drugs has been reported.

Efforts have been made to provide drug dosage forms that may increase the compliance of patients and thereby lower the rate of relapse in the treatment of schizophrenia. U.S. Pat. No. 7,807,680 and U.S. Publication No. 2005/0032811 describe long-acting aripiprazole sterile injectable formulations. Studies on aripiprazole free base injections showed a prolonged pharmacokinetic profile, but incidents of unacceptable (moderate to severe) tissue irritation following IM and SC injection were also reported.

U.S. Pat. No. 7,115,587 discloses an injectable formulation that delivers an aripiprazole solution complexed with a substituted β-cyclodextrin to the muscular site with diminished irritation as compared to injectable suspensions containing uncomplexed aripiprazole. The Abilify® injection for intramuscular use is a single-dose, ready to use vial consisting of 9.75 mg/1.3 ml of aripiprazole and 150 mg/ml of sulfobutylether β-cyclodextrin. Formulation challenges due to drug loading and poor solubility of aripiprazole in β-cyclodextrin at neutral pH have been reported.

Olanzapine (1,2-methyl-4-(4-methyl-1-piperazinyl)-10H-thieno[2,3-b][1,5]benzodiazepine) is a second generation antipsychotic drug marketed as Zyprexa®. It is useful for the treatment of disorders such as schizophrenia, bipolar disorder, psychotic depression and Tourette syndrome. This active pharmaceutical ingredient acts as an antagonist on 5-$HT_2$ serotonin receptors as well as the $D_1/D_2$ dopamine receptors, while also exhibiting anticholinergic and antimuscarinic properties. Olanzapine belongs to the benzodiazepine family, and has the following structure:

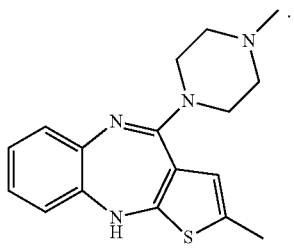 [SMILES: Cc1cc2c(s1)Nc1ccccc1N=C2N1CCN(C)CC1]

This compound is disclosed, for example, in U.S. Pat. Nos. 5,229,382 and 6,169,084. An extended release intramuscular injection product containing the water-insoluble salt olanzapine pamoate monohydrate is approved for use in schizophrenia. Like aripiprazole, olanzapine can cause adverse site reactions when injected into a subject.

SUMMARY OF THE INVENTION

There exists a need for improved pharmaceutical compositions of aripiprazole, olanzapine, prodrugs thereof, and other anti-psychotic agents, for extended release use, thereby improving patient compliance and optimizing the pharmacological profile of the active agent.

Provided herein are pharmaceutical compositions comprising (a) a water-insoluble antipsychotic agent, and (b) sorbitan esters of a carboxylic acid, wherein the carboxylic acid comprises 8-14 carbon atoms. In a particular embodiment, the sorbitan ester is sorbitan laurate (SML). In an embodiment, the composition can be in the form of an aqueous, flocculated, injectable suspension. The composition can comprise additional components, such as a polyoxyethylene derivative of a sorbitan ester of a carboxylic acid, wherein the carboxylic acid comprises 8-14 carbon atoms (e.g., polysorbate 20). The pharmaceutical composition can be injectable.

These pharmaceutical compositions can take a variety of forms. Such forms include, but are not limited to, completely dispersed and flocculated systems.

As described below, the pharmaceutical compositions described herein have a number of advantages. For example, the compositions can be easily resuspended by the user, e.g., through handshaking, in a short time prior to administration. In another example, the pharmaceutical compositions, e.g., flocculated systems, can be used to improve the local tissue reaction of antipsychotic drugs in extended release formulations. By mitigating the adverse results associated with the injection of these drugs, drug compliance will be greatly improved.

Water insoluble antipsychotic agents that can be used in the pharmaceutical compositions described herein include aripiprazole, as well as prodrugs thereof, and olanzapine, as well as prodrugs thereof. Particular prodrugs of aripiprazole include compounds of the formula (I) or formula (II), e.g., compounds of the formula (I'), e.g., compounds A-4 and A-7:

Particular prodrugs of olanzapine include compounds of the formula (III) or (IV):

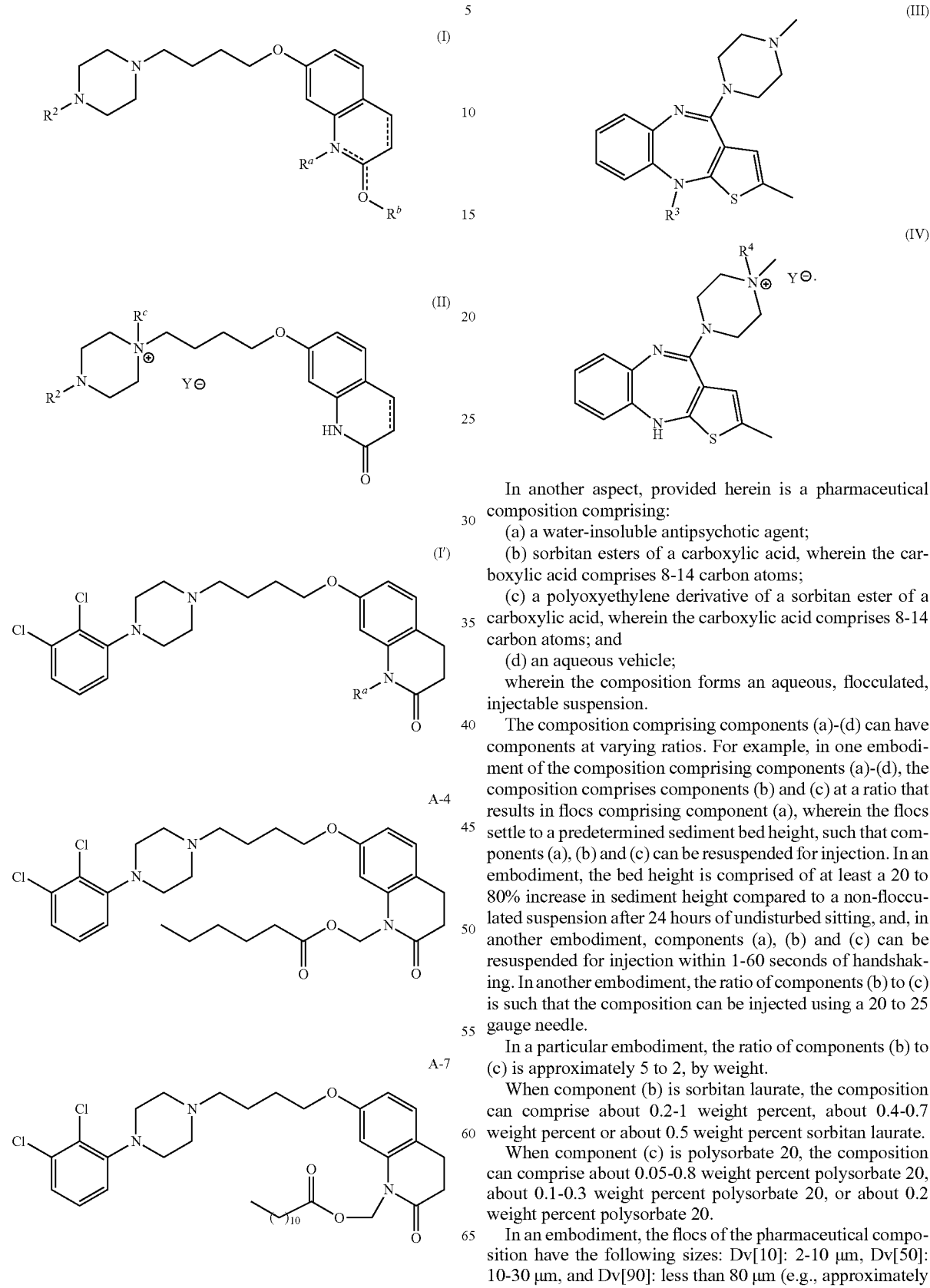

In another aspect, provided herein is a pharmaceutical composition comprising:

(a) a water-insoluble antipsychotic agent;

(b) sorbitan esters of a carboxylic acid, wherein the carboxylic acid comprises 8-14 carbon atoms;

(c) a polyoxyethylene derivative of a sorbitan ester of a carboxylic acid, wherein the carboxylic acid comprises 8-14 carbon atoms; and (d) an aqueous vehicle;

wherein the composition forms an aqueous, flocculated, injectable suspension.

The composition comprising components (a)-(d) can have components at varying ratios. For example, in one embodiment of the composition comprising components (a)-(d), the composition comprises components (b) and (c) at a ratio that results in flocs comprising component (a), wherein the flocs settle to a predetermined sediment bed height, such that components (a), (b) and (c) can be resuspended for injection. In an embodiment, the bed height is comprised of at least a 20 to 80% increase in sediment height compared to a non-flocculated suspension after 24 hours of undisturbed sitting, and, in another embodiment, components (a), (b) and (c) can be resuspended for injection within 1-60 seconds of handshaking. In another embodiment, the ratio of components (b) to (c) is such that the composition can be injected using a 20 to 25 gauge needle.

In a particular embodiment, the ratio of components (b) to (c) is approximately 5 to 2, by weight.

When component (b) is sorbitan laurate, the composition can comprise about 0.2-1 weight percent, about 0.4-0.7 weight percent or about 0.5 weight percent sorbitan laurate.

When component (c) is polysorbate 20, the composition can comprise about 0.05-0.8 weight percent polysorbate 20, about 0.1-0.3 weight percent polysorbate 20, or about 0.2 weight percent polysorbate 20.

In an embodiment, the flocs of the pharmaceutical composition have the following sizes: Dv[10]: 2-10 μm, Dv[50]: 10-30 μm, and Dv[90]: less than 80 μm (e.g., approximately 65 um). In another embodiment, the flocs are Dv[10]: 1-10 μm, Dv[50]: 5-30 μm, and Dv[90]: less than 65 μm.

The compositions can have varying amounts of antipsychotic agent in the pharmaceutical composition. For example, the composition can be comprised of 15-35 weight percent, e.g., 20-30 weight percent, e.g., 20-26 weight percent aripiprazole, or olanzapine, or a compound of formula I, II, III, IV or V (lurasidone).

In another aspect, provided herein is an aqueous injectable suspension comprising:

(a) aripiprazole, or olanzapine, or a compound of formula I, II, III, IV or V, pharmaceutically acceptable salts, hydrates, or solvates thereof,
wherein component (a) is in a weight ratio of approximately 15-35%;
(b) sorbitan laurate in a weight ratio of approximately 0.2-1%
(c) polysorbate 20 in a weight ratio of approximately 0.05-0.8%; and
(d) an aqueous carrier.

In one embodiment of the aqueous injectable suspension, the components are as follows:

(a) aripiprazole, or olanzapine, or a compound of formula I, II, III, IV or V in a weight ratio of approximately 20-26%;
(b) sorbitan laurate in a weight ratio of approximately 0.5%;
(c) polysorbate 20 in a weight ratio of approximately 0.2%; and
(d) an aqueous carrier.

In one embodiment, the pharmaceutical composition is formulated for use in delivering a water-insoluble antipsychotic agent into a host. In a preferred embodiment, the host is human. The composition can be intended for parenteral (e.g., intramuscular, intradermal or subcutaneous) administration. In certain embodiments, the composition is formulated for delivery through a needle into a host. Accordingly, the composition may be formulated for delivery for injection through a syringe equipped with a needle, where the end-user resuspends the composition prior to use.

In an embodiment, the antipsychotic agent (e.g., aripiprazole, or olanzapine, or a compound of formula I, II, III, IV or V) can be formulated for modulating tissue reaction associated with the delivery of a water-insoluble antipsychotic agent. The pharmaceutical composition having reduced injection site reaction can comprise (a) an antipsychotic agent, and (b) sorbitan esters of a carboxylic acid, wherein the carboxylic acid comprises 8-14 carbon atoms. In a particular embodiment, the sorbitan ester is sorbitan laurate. In an embodiment, the composition for injection site modulation can comprise additional components, such as a polyoxyethylene derivative of a sorbitan ester of a carboxylic acid, wherein the carboxylic acid comprises 8-14 carbon atoms (e.g., polysorbate 20).

In another embodiment, the modulation of the tissue reaction is a reduction in the irritation at the site of injection. In another embodiment, the modulation of the tissue reaction is a reduction in the irritation following IM or SC injection. In certain embodiments, the tissue reaction is reduced by at least about 20 percent by weight. In other embodiments, the tissue reaction is reduced by at least about 10 percent by weight.

In one embodiment, the antipsychotic agent is selected from the group consisting of aripiprazole, or olanzapine, or a compound of formula I, II, III, IV or V and pharmacologically active salts, hydrates or solvates thereof In certain embodiments, the pharmaceutical composition for injection site reaction modulation further comprises a buffer. The buffer may be selected from a phosphate, citrate, tartrate or acetate buffer. In a particular embodiment, the buffer is a phosphate buffer.

In a particular embodiment of the preceding compositions, the composition comprises a water-insoluble antipsychotic agent, about 0.1-2% percent of sorbitan laurate, about 0.05-1% percent of polysorbate 20 and phosphate buffer. In a particular embodiment, the phosphate buffer comprises isotonic saline with 5-50 mM phosphate buffer at pH 5.0-7.5.

In another aspect, provided herein is an injectable composition comprising sorbitan laurate, polysorbate 20, phosphate buffer and aripiprazole, or pharmacologically active salts, hydrates, solvates or prodrugs thereof.

In yet another aspect, provided herein is an injectable composition comprising sorbitan laurate, polysorbate 20, phosphate buffer and olanzapine, or pharmacologically active salts, hydrates, solvates or prodrugs thereof.

In yet another aspect, provided herein is an injectable composition comprising sorbitan laurate, polysorbate 20, phosphate buffer and Compound A-7, or pharmacologically active salts, hydrates, solvates or prodrugs thereof.

Also provided herein is a method for treating disorders of the central nervous system, comprising administering an effective amount of any of the preceding compositions to an individual in need of such treatment.

In one embodiment, the disorder is anxiety or depression. In another embodiment, the disorder is bipolar disorder. In still another embodiment, the disorder is autism-related irritability. In yet another embodiment, the disorder is a psychotic condition. The psychotic condition may be schizophrenia or schizophreniform diseases. Alternatively, the psychotic condition may be acute mania.

In still another aspect, provided herein is a method of modulating tissue reaction associated with delivering a water-insoluble antipsychotic agent through a needle into a host, comprising a water-insoluble antipsychotic agent and sorbitan laurate. In one embodiment of the method, the composition is administered parenterally. In certain embodiments, the composition is administered intradermally, subcutaneously or intramuscularly. In another embodiment of the method, the modulation of the tissue reaction is a reduction in the irritation and the subsequent granuloma formation at the site of injection. In a certain embodiments, the tissue reaction is reduced by at least about 20 percent. In other embodiments, the tissue reaction is reduced by at least about 10 percent. In still another embodiment of the method, the composition comprises a water-insoluble antipsychotic agent, about 0.1-2% percent of sorbitan laurate, about 0.05-1% percent of polysorbate 20 and phosphate buffer.

BRIEF DESCRIPTION OF THE FIGURES

FIG. 1 shows results from the settled bed height assessments described in the experimental section. The data indicate that pharmaceutical compositions containing sorbitan laurate and polysorbate 20 have significantly higher settled bed heights than compositions without sorbitan laurate.

FIG. 2 shows sorbitan laurate's positive effect on settled bed height in pharmaceutical compositions of antipsychotic drugs.

FIG. 3 shows an example photograph illustrating the sediment height measurement on a vial for the pharmaceutical compositions described herein.

FIG. 4 shows microscopy images of three suspensions made with pharmaceutical compositions containing polysorbate 20 and increasing amounts of sorbitan laurate. It is visually clear that flocculation is occurring as SML content in the vehicle increases.

FIG. 5 shows vials containing pharmaceutical compositions after sedimentation with sediment height calculations.

FIG. 6 shows plots of pharmaceutical composition re-suspension time vs. drug particle size. Larger measured suspension particle sizes, caused by flocculation, facilitate faster re-suspension than smaller ones.

FIG. 7 is a contour plot showing amounts of polysorbate 20 and sorbitan laurate necessary for adequate wetting and re-suspendability.

Figure 8B:
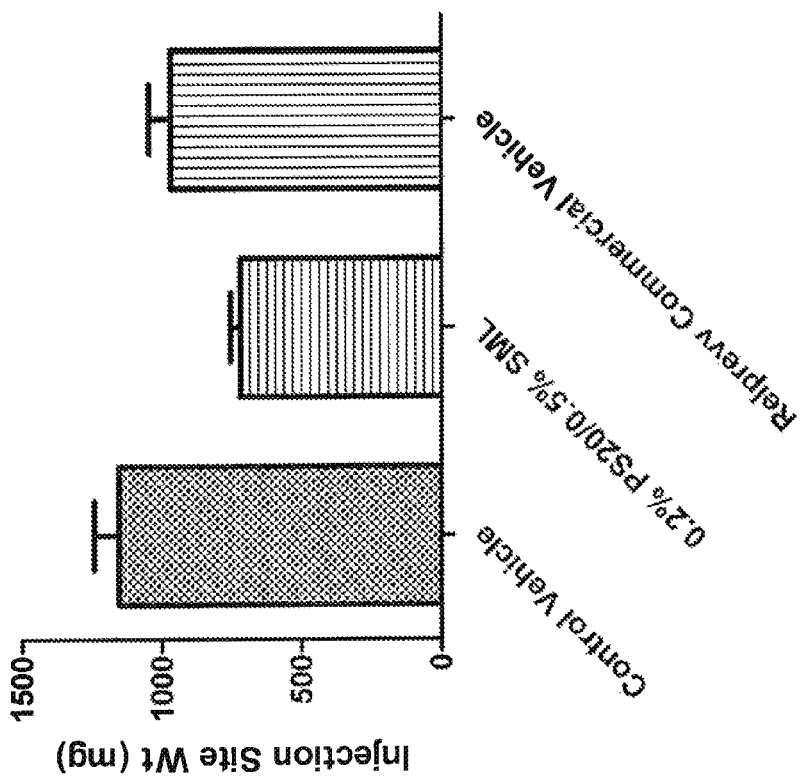

FIGS. 8A and 8B demonstrate the reduction of tissue reaction associated with antipsychotic drugs when the drugs are formulated with sorbitan laurate.

FIG. 9 demonstrates the results of solubility studies comprising varying ratios of active agent, component (b), and component (c).

DETAILED DESCRIPTION OF INVENTION

Pharmaceutical Compositions

Provided herein is an injectable pharmaceutical composition comprising an antipsychotic agent and a sorbitan ester of a carboxylic acid, wherein the carboxylic acid comprises 8-14 (e.g., 11-13) carbon atoms. A preferred sorbitan ester is sorbitan laurate. This composition is particularly useful for the formulation of a water-insoluble antipsychotic agent into an injectable pharmaceutical composition. In addition to a sorbitan ester of a carboxylic acid, the pharmaceutical composition can further comprise a polyoxyethylene derivative of a sorbitan ester of a carboxylic acid, wherein the carboxylic acid comprises 8-14 carbon atoms. In an embodiment, the polyoxyethylene derivative is polysorbate 20. The pharmaceutical composition can further comprise and aqueous vehicle, such as phosphate buffered saline, as well as any of the pharmaceutical components described herein.

The compositions described herein possess a number of advantages. For example, the compositions offer minimized excipient levels while co-optimizing both re-suspendability and acceptable injectability, and maintain good physiochemical attributes of the antipsychotic agent. As described in the experimental section, these properties were discovered based on comparisons of vehicle performance based on settled bed height and qualitative ease of resuspension. Briefly, the redispersibility of the pharmaceutical compositions were assessed by preparing a number of different formulations (antipsychotic agent with a variety of excipients), and comparing the relative height of the settled beds. In general, higher settled bed heights are indicative of flocculated, or loosely aggregated, particles. These suspensions settle faster initially, but their loosely aggregated state allows for easier redispersion and better physical stability as the particles cannot pack as tightly as fully dispersed suspensions, thereby leading to reduced resuspension times using, for example, hand shaking. In one embodiment, the pharmaceutical compositions, e.g., a pharmaceutical composition of components (a) and (b), or (a), (b) and (c), can be resuspended for injection within 1-60 seconds of handshaking.

As used herein, the term "flocculation" refers to the formation of a loose aggregation of discrete particles held together in a network-like structure by physical adsorption of macromolecules, bridging during chemical interaction (precipitation), or when the longer range van der Waals forces of attraction exceed the shorter range forces of attraction. (See Pharmaceutical dosage forms: Disperse systems Volume 2. Edited by Herbert A. Lieberman, Martin M. Rieger, and Gilbert S. Banker. (1996) Pg. 18). The "loose aggregation of discrete particles" can be referred to herein as "flocs."

As shown in FIG. 1, pharmaceutical compositions containing component (b) (e.g., sorbitan laurate) and component (c) (e.g., polysorbate 20) have significantly higher settled bed heights than compositions without component (b), regardless of the presence of additional additives (e.g., polymers) or salts (e.g., phosphate buffer, saline). Additionally, the flocculation induced is unique to component (b)/component (c), as evidenced by comparison to compositions containing sorbitan monopalmitate, docusate sodium, or polysorbate 20 alone. As described below, the flocculation phenomenon is uniquely attributed to the additional influence of component (b), e.g., sorbitan laurate.

Accordingly, in one embodiment, provided herein is a composition comprising components (a), (b) and (c) at a ratio that results in flocs, wherein the flocs settle to greater than a predetermined sediment bed height, such that components (a), (b) and (c) can be resuspended for injection. The flocs can be comprised of component (a), components (a) and (b), or components (a), (b) and (c). A predetermined sediment bed height refers to a bed height that is higher than the bed height of a comparative pharmaceutical composition that has none of component (b), or none of components (b) or (c). In one embodiment, the bed height is comprised of at least a 10, 20, 30, 40, 50, 60, 70 or 80% increase in sediment height compared to a non flocculated pharmaceutical composition after 24 hours of undisturbed sitting. In another embodiment, the bed height is comprised of at least a 20 to 80% increase in sediment height compared to a non flocculated pharmaceutical composition after 24 hours of undisturbed sitting.

The formed flocs can be any number of sizes. Non-limiting examples of sizes include Dv[10]: 2-10 μm, Dv[50]: 10-30 μm, and Dv[90]: less than 80 μm (e.g., approximately 65 um). In another embodiment, the flocs are Dv[10]: 1-10 μm, Dv[50]: 5-30 μm, and Dv[90]: less than 65 μm.

In addition to the re-suspendability and injectability advantages described above, the pharmaceutical compositions provided herein result in reduced tissue reactions. Typically, flocculated pharmaceutical suspensions have an increased viscosity and reduced flow properties, which impact the ability to inject or administer the product to the patient. This in turn may negatively impact the local tissue response; therefore it is surprising that the formulations described herein result in improved tissue response.

Accordingly, in one embodiment, provided herein is a method of modulating tissue reactions associated with delivering a water-insoluble antipsychotic agent into a host, comprising the water-insoluble antipsychotic agent and component (b), e.g., sorbitan laurate. In another embodiment, the antipsychotic agent/component (b) composition is delivered to the host through a needle.

Surprisingly, it has been discovered that the composition provided herein results in a decreased tissue reaction normally associated with antipsychotic agents, such as aripiprazole, olanzapine, derivatives thereof, prodrugs thereof, and salts thereof. As demonstrated in the experimental section, an injectable composition comprising an antipsychotic agent and a sorbitan ester of a carboxylic acid, wherein the carboxylic acid comprises 8-14 carbon atoms (e.g., sorbitan laurate), demonstrated an unexpected improvement in tissue reaction compared to a similar compositions comprising a sorbitan ester of a carboxylic acid falling outside of this range (e.g., sorbitan monopalmitate). Without being bound by theory, it is believed that a favorable surface interaction between the sorbitan ester of a carboxylic acid (e.g., sorbitan laurate) and the antipsychotic drug (e.g., aripiprazole or olanzapine) reduces tissue reaction.

Moreover, due to the maximized interaction between these components, the injectable composition provided herein can be formulated and maintained in suspension with ease. Surprisingly, it was found that it was easier to formulate the antipsychotic drugs described herein using a sorbitan ester of a carboxylic acid, wherein the carboxylic acid comprises 8-14 carbon atoms (e.g., sorbitan laurate) compared with other sorbitan esters falling outside of this range (e.g., sorbitan monopalmitate). This was also unexpected. Without being bound by theory, it is believed that the sorbitan ester component of the injectable composition provided herein improves the hydrophilicity of the drug through surface interactions of the various components. It is additionally noted that formulation vehicles containing sorbitan laurate and polysorbate 20 formed visible emulsions with no oiling out of either surfactant. In contrast, formulations containing sorbitan palmitate, did not form consistent emulsions, even with the addition of a second non-ionic surfactant, with visible undissolved material at the bottom of the material.

As used herein, the term "tissue reaction" (TR) refers to foreign body responses to a drug product (active agent and/or vehicle used for administration). For example, local tissue reaction to drug product results in the influx of immune cells, the subsequent encapsulation of the drug product and usually the development of a fluid filled central cavity. The presence of fibroblasts, neutrophils, macrophages and giant cells are often observed via histological examination. The term "undue TR" or "unacceptable TR" refers to moderate to severe TR which is unacceptable to the patient and thereby impacts unfavorably on patient comfort and compliance. The term "reduced TR" refers to generally minimal to mild TR which is acceptable to the patient and therefore does not engender an adverse event related nor impact unfavorably on patient compliance. As such, the injectable composition provided herein is characterized by a decreased undue TR and a more acceptable TR following injection of drug product. As used herein, "tissue reaction" can also be referred to as "injection site reaction."

The modulation of tissue response following SC administration is described by the reduction of the injection site weight (comprising the drug depot and surrounding tissue) which provides a quantitative assessment of the severity of the response. The modulation of the tissue response following IM administration is described by the spreadability of the drug and resulting depot morphology; spreading of the drug along the fascial planes of muscle is desirable rather than the formation of a concentrated mass of drug in a small area.

Depot morphology resulting from IM injection of aripiprazole and aripiprazole prodrugs has been described. Injections of slow-releasing formulations of drugs, including aripiprazole commonly result in the formation of "cyst-like structures", characterized by a vascularized capsule of roughly spherical shape and comprising various cell types, with or without and a central serous fluid compartment. Tissue responses to slow-releasing formulations occur as the body mounts an immune response to clear the material from the injection site; this reaction is commonly referred to as a foreign body response. The spherical nature of these reactions can result in localized discomfort and pain, as the FBR increases in size compressing on nerve fibers innervating muscle tissue and with the release of pro-inflammatory cytokines from the site.

In a particular embodiment, the modulation of the tissue reaction is the reduction in tissue reaction at the site of injection. In one embodiment, the injection site reaction is reduced by a particular amount, e.g., about 90%, 80%, 70%, 60%, 50%, 40%, 30%, 20%, 10%, 5%, etc.

When the antipsychotic agent/sorbitan ester composition is to be used as an injectable composition, including but not limited to injection through a needle or needle-less injection, it can be formulated into a conventional injectable carrier. Suitable carriers include biocompatible and pharmaceutically acceptable solutions.

Provided below are representative drawings of the sorbitan esters used in the pharmaceutical compositions described herein. Sorbitan laurate can also be referred to as "sorbitan monolaurate":

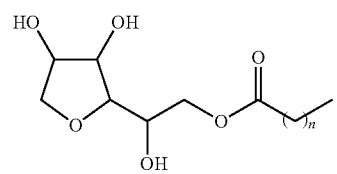

Sorbitan Ester $n = 6-12$

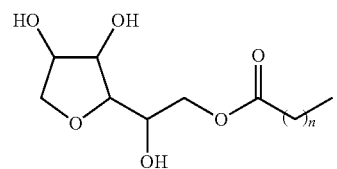

Sorbitan Laurate ($n = 10$)

As described above, the pharmaceutical composition comprising components (a) and (b) can further comprise component (c): a polyoxyethylene derivative of a sorbitan ester of a carboxylic acid, wherein the carboxylic acid comprises 8-14 carbon atoms. In a particular embodiment, component (c) is polysorbate 20, sold under the trademark TWEEN®. The polysorbate can be added in an amount that reduces surface tension of a drug product or aids in suspension stability of the drug product.

Provided below are representative drawings of the polyoxyethylene derivative of a sorbitan ester of a carboxylic acid used in the pharmaceutical compositions:

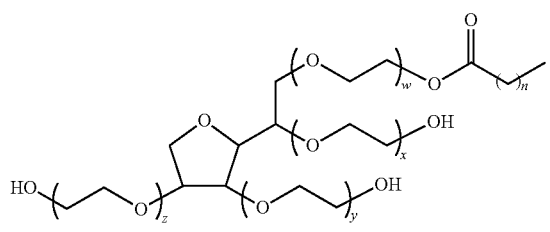

Polyoxyethylene Derivative of a Sorbitan Ester
$w + x + y + z = 20$
$n = 6-12$

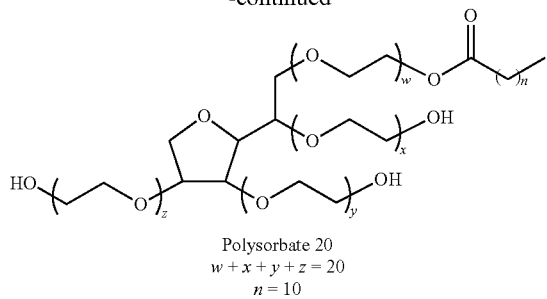

Polysorbate 20
$w + x + y + z = 20$
$n = 10$

For compositions comprising components (a), (b), and (c), or (a), (b), (c) and (d), the ratios of (b) and (c) can vary. In one embodiment, the ratio of components (b) to (c) is approximately 10 to 0.5, e.g., 10 to 1, e.g., 8 to 1, e.g., 5:2, by weight. In another embodiment, the ratio of components (b) to (c) is approximately 5 to 2, by weight. In still another embodiment, the composition comprises component (a), sorbitan laurate, and polysorbate 20, wherein the ratio of sorbitan laurate and polysorbate 20 is approximately 5 to 2, by weight. In still another embodiment, the composition comprises component (a), sorbitan laurate, and polysorbate 20, wherein the ratio of sorbitan laurate and polysorbate 20 is approximately 3 to 1, by weight. In another embodiment, the composition comprises component (a), sorbitan laurate, and polysorbate 20, wherein the ratio of sorbitan laurate and polysorbate 20 is approximately 2 to 1, by weight. In yet another embodiment, the composition comprises component (a), sorbitan laurate, and polysorbate 20, wherein the ratio of sorbitan laurate and polysorbate 20 is within the range of approximately 3 to 1-2 to 1, by weight.

As described in Table 3, the sorbitan laurate/polysorbate 20 ratio can be approximately 0.625, 1, 1.25, 2, 2.5, or 5, representing a range of 0.625-5.

For compositions comprising components (a) and (b), (a), (b), and (c), or (a), (b), (c) and (d), the weight percent of (b) and (c) can vary. In one embodiment, the composition comprises about 0.2-1 weight percent component (b), e.g., sorbitan laurate. In another embodiment, the composition comprises about 0.4-0.7 weight percent component (b), e.g., sorbitan laurate. In still another embodiment, the composition comprises about 0.5 weight percent component (b), e.g., sorbitan laurate.

In another embodiment, the composition comprises about 0.05-0.8 weight percent component (c), e.g., polysorbate 20. In yet another embodiment, the composition comprises about 0.1-0.3 weight percent component (c), e.g., polysorbate 20. In still another embodiment, the composition comprises about 0.2 weight percent polysorbate 20.

In an embodiment, the ratio of components (b) to (c) is such that the composition can be injected using a 20-25 gauge needle. For example, the needle can be a 20, 21, or 23.5 gauge needle.

The compositions provided herein can also have varying amounts of antipsychosis agent. The antipsychosis agent can be aripiprazole, or olanzapine, salts of these compounds, hydrates of these compounds, and/or prodrugs of these compounds. In one embodiment, the composition comprises approximately 15-35 weight percent aripiprazole, or olanzapine, or a compound of formula I, II, III, IV or V (lurasidone), or pharmaceutically acceptable salts, hydrates, or solvates thereof. In another embodiment, the composition comprises approximately 20-30 weight percent aripiprazole, or olanzapine, or a compound of formula I, II, III, IV or V, or pharmaceutically acceptable salts, hydrates, or solvates thereof. In still another embodiment, the composition comprises approximately 20-26 weight percent aripiprazole, aripiprazole, or olanzapine, or a compound of formula I, II, III, IV or V, or pharmaceutically acceptable salts, hydrates, or solvates thereof. In another embodiment, the composition comprises approximately 24-26 weight percent aripiprazole, or olanzapine, or a compound of formula I, II, III, IV or V, or pharmaceutically acceptable salts, hydrates, or solvates thereof.

The aqueous vehicle of the pharmaceutical compositions provided herein can be a buffer. The buffer may be selected from a phosphate, citrate, tartrate or acetate buffer. In a particular embodiment, the buffer is a phosphate buffer.

The pharmaceutical compositions provided herein can further comprise additional components. For example, the use of additional wetting agents or surfactants in a pharmaceutical composition may promote one or more of the following:

(1) Surface tension reduction, which may aid in wetting, since a 'lower surface tension' liquid will wet surfaces or particles more readily than a 'high surface tension' liquid. Lowering the surface tension of a liquid may also decrease the incidence of foaming. The surface tension of a liquid will be lower as more surfactant is added;

(2) Formation of micelles (i.e., spherical or non-spherical surfactant structures in solution that have the capability to dissolve non-soluble components); and/or (3) Increase of suspension physical stability.

The pharmaceutical compositions can also contain an aqueous vehicle, which is a vehicle that dilutes and suspends the drug. The diluent of interest herein is one which is pharmaceutically acceptable (safe and non-toxic for administration to a human) and is useful for the preparation of a reconstituted formulation. Exemplary diluents include sterile water, sterile water for injection (WFI), bacteriostatic water for injection (BWFI), a pH buffered solution (e.g., phosphate-buffered saline), sterile saline solution, Ringer's solution or dextrose solution. The buffer can be phosphate, citrate, tartrate or acetate. In a particular embodiment, the diluent is phosphate-buffered saline, which is a water-based salt solution containing either sodium chloride or potassium chloride, and sodium phosphate or potassium phosphate. In one embodiment, the phosphate buffer comprises isotonic saline with 5-50 mM phosphate buffer at pH 4.0-9.0, e.g., 5.0-8.0, e.g., 5.0-7.5.

The pharmaceutical compositions can further contain an additional surfactant that preferentially adsorbs to an interface between two immiscible phases, such as the interface between water and an organic polymer solution, a water/air interface or organic solvent/air interface. Suitable surfactants include but are not limited to fatty alcohols such as polyethylene glycols (PEGs) and cetyl alcohol.

Optionally, the pharmaceutical compositions can further comprise a dispersant, such as, for example, carboxymethyl cellulose (CMC), carboxymethyl cellulose sodium, crosslinked sodium carboxymethyl cellulose, calcium carboxymethyl cellulose, and low substituted hydroxypropyl cellulose magnesium aluminum silicate, or a mixture thereof. In a particular embodiment, the pharmaceutical composition comprises carboxymethyl cellulose.

The pharmaceutical compositions may also optionally comprise an antioxidant to inhibit the oxidation of ingredients. Some examples of antioxidants include, but are not limited to, ascorbic acid, ascorbyl palmitate, butylated hydroxyanisole, a mixture of 2 and 3 tertiary-butyl-4-hydroxyanisole, butylated hydroxytoluene, sodium iso-ascorbate, dihydroguaretic acid, potassium sorbate, sodium bisulfate, sodium metabisulfate, sorbic acid, potassium ascorbate, vitamin E, 4-chloro-2,6-ditertiary butylphenol, alpha-tocopherol, and propylgallate.

The pharmaceutical compositions can further include a lipid, e.g., a neutral lipid. Neutral lipids include any lipid that remains neutrally charged at a pH between about 4 and 9. Neutral lipids include, without limitation, cholesterol, other sterols and derivatives thereof, phospholipids, and combinations thereof and other neutral lipids. The phospholipids include any one phospholipid or combination of phospholipids capable of forming liposomes. They include phosphatidylcholines, phosphatidylethanolamines, lecithin and fractions thereof, phosphatidic acid, phosphatidylglycerols, phosphatidylinositols, phosphatidylserines, plasmalogens and sphingomyelins. The phosphatidylcholines include, without limitation, those obtained from egg, soy beans or other plant sources or those that are partially or wholly synthetic or of variable lipid chain length and unsaturation, POPC, OPPC, natural or hydrogenated soy bean PC, natural or hydrogenated egg PC, DMPC, DPPC, DSPC, DOPC and derivatives thereof. In one embodiment, phosphatidylcholines are POPC, non-hydrogenated soy bean PC and non-hydrogenated egg PC. Phosphatidylethanolamines include, without limitation, DOPE, DMPE and DPPE and derivatives thereof. Phosphatidylglycerols include, without limitation, DMPG, DLPG, DPPG, and DSPG. Phosphatidic acids include, without limitation, DSPA, DMPA, DLPA and DPPA.

The pharmaceutical compositions can also advantageously employ a density enhancing agent, such as a sugar, e.g., mannitol, or sorbitol and/or a tonicity adjusting agent, such as sodium chloride or glycerol.

Other pharmaceutical carriers that could be used in the pharmaceutical compositions provided herein also include water, aqueous methylcellulose solutions, saline, dextrose solutions, fructose solutions, ethanol, or oils of animal, vegetative, or synthetic origin. The pharmaceutical carrier may also contain preservatives, and buffers as are known in the art.

The term "pharmaceutical composition", "formulation", "injectable composition," etc. are used synonymously throughout the application.

The pharmaceutical compositions described herein may also be in the form of an emulsion. The term "emulsion" as used in this specification denotes a two-phase system in which one phase is finely dispersed in the other phase. An emulsifier can be used in the pharmaceutical compositions to form the emulsion. The term emulsifier, as used by this invention, denotes an agent that can reduce and/or eliminate the surface and the interfacial tension in a two-phase system. Such an agent possesses both hydrophilic and lipophilic groups in the emulsifier agent.

The pharmaceutical compositions described herein may also be in the form of a dispersion. As used herein, the term "dispersion" is to be understood as a mixture in which fine particles of one substance (e.g., a drug) are scattered throughout another substance (e.g., a liquid). Dispersions include suspensions, and colloids.

The methods of the invention include administering the compositions described herein, thereby obtaining an extended release or sustained release profile in the patient. "Extended-release" or "sustained-release" includes dosage forms whose drug-release characteristics of time course and/or location are chosen to accomplish therapeutic or convenience objectives not offered by conventional dosage forms such as a solution or an immediate release dosage form. An extended release profile includes deliveries that achieve a therapeutically effective amount of the antipsychotic agent, e.g., aripiprazole, or olanzapine, or a compound of formula I, II, III, IV or V, is present in the plasma of the individual for at least about 7 days, preferably at least about 14 days, or more preferably at least about 21 days alternatively for at least 2, 3, 4, 6 or 8 weeks or as much as three months.

In one embodiment, the pharmaceutical compositions can be administered as a single or sole (undivided) dose. However, the composition is also useful for those individuals that require constant or chronic therapy, such as those that receive repeated doses over several hours, days, weeks, months, or more. In such dosing regimens, the method can comprise a first administration of a first extended release composition and a second administration of a second extended release composition. The second composition can be the same, substantially the same or different as the first and can include the same active agent or a different active agent. For example, the second composition can be administered at about 7 days, or more, such as at least about 14 days, or at least about 17 days, after the first administration, where the first administration results in the release of agent for a period of 1, 2, 3, 4, 5, 6, 7, 8, 9, 10, 11, 12, 13, 14 days, or more.

The injectable, pharmaceutical compositions described herein can be injected into a patient in any number of ways. The term "injectable" as used herein refers to a composition that is suitable to be delivered to an individual in an injection, such as with an injection device, including one that employs a syringe or a cartridge, which may be housed in a manual injection device or an auto-injection device, for example. Specifically, the injectable composition is suitable for parenteral administration. As used herein, the term "parenteral administration" refers to administration through injection or infusion. Parenteral administration includes, but is not limited to, intravenous administration, intradermal administration, subcutaneous administration or intramuscular administration. The term "intravenous administration" means administration into a vein. "Intradermal administration" is injection into the upper layer of skin (i.e., the dermis), just beneath the epidermis. "Subcutaneous administration" refers to administration just below the skin. "Intramuscular administration" is the injection directly into a muscle.

Antipsychotic Agents

As discussed above, the pharmaceutical compositions provided herein are useful for the administration of antipsychotic drugs to a subject. As used herein the term "antipsychotic" refers all drugs used to treat psychosis. Common conditions for which antipsychotics are prescribed include schizophrenia, mania and delusional disorder, although antipsychotics are also used to counter psychosis associated with a wide range of other diagnoses. Antipsychotics also act as mood stabilizers making them suitable for the treatment of bipolar disorder (even when no symptoms of psychosis are present). The pharmaceutical compositions provided herein are particularly useful for formulating a water-insoluble antipsychotic into an injectable composition.

The pharmaceutical compositions described herein are useful for administration of water-insoluble antipsychotic agents. As used herein, a water-insoluble antipsychotic agent is one that dissolves in a quantity of water to an extent of less than 100%. The term "water-insoluble" does not necessarily refer to complete or 100% water-insolubility. In certain embodiments, the water-insoluble material dissolves to an extent of less than 50%. In other embodiments, the water-insoluble material dissolves to an extent of less than 10%. In a particular embodiment, the water-insoluble material dissolves to an extent of less than 1%. The term "water-insoluble" can refer to solubility as prescribed in the United States Pharmacopoeia.

In one embodiment, the antipsychotic drug of the pharmaceutical composition is aripiprazole. The aripiprazole drug substance can comprise, consist essentially of, or consist of aripiprazole (in a crystalline, non-crystalline or amorphous form), an aripiprazole salt, an aripiprazole solvate (including ethanolates and hydrates), or other aripiprazole polymorphs. Preferred salts include those salts insoluble in an aqueous vehicle. Pharmaceutical salts such as the hydrochloride and various pharmaceutically acceptable carboxylate salts are suitable.

The aripiprazole drug substance can also include aripiprazole prodrugs. The term "prodrug" is art-recognized and is intended to encompass compounds which, under physiological conditions, are converted into active compounds, e.g., those described herein. A common method for making a prodrug is to select moieties which are hydrolyzed or otherwise cleaved under physiological conditions to provide the desired compound. In other embodiments, the prodrug is converted by an enzymatic activity of the host animal.

Preferred aripiprazole prodrugs that can be used in the pharmaceutical compositions include the prodrugs described in U.S. Publication No. 2011/0003828, which is incorporated herein by reference in its entirety.

In a particular embodiment, the aripiprazole prodrug is a compound of formula (I) or formula (II):

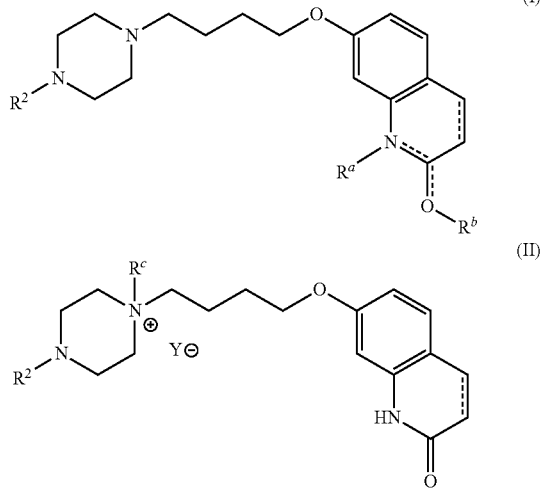

wherein $R^a$ is absent, and $R^b$ is —CH$_2$OC(O)R$^1$, —CH$_2$OC(O)OR$^1$, —CH$_2$OC(O)N(R$^1$)$_2$ or —C(O)R$^1$;

or $R^b$ is absent, and $R^a$ is —CH$_2$OC(O)R$^1$, —CH$_2$OC(O)OR$^1$, —CH$_2$OC(O)N(R$^1$)$_2$ or —C(O)R$^1$;

$R^c$ is —CH$_2$OC(O)R$^1$, —CH$_2$OC(O)OR$^1$, —CH$_2$OC(O)N(R$^1$)$_2$ or —C(O)R$^1$;

wherein each R$^1$ is independently selected from the group consisting of hydrogen, substituted or unsubstituted aliphatic, and substituted or unsubstituted aryl; and wherein each R$^2$ is selected from the group consisting of substituted or unsubstituted aryl and substituted or unsubstituted heteroaryl;

wherein Y$^\ominus$ is a pharmaceutically acceptable counterion; and wherein ═══ represents a single or double bond.

Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.

In one embodiment of formula (I), the aripiprazole prodrug is a compound of formula (I'):

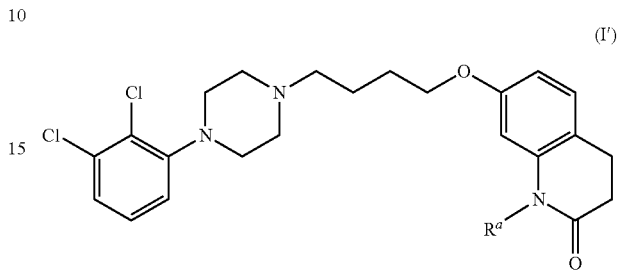

wherein R$^a$ is CH$_2$OC(O)R$^1$ and wherein R$^1$ is selected from substituted or unsubstituted aliphatic.

In a particular embodiment of formula (I'), R$^1$ is —CH$_2$OC(O)—(CH$_2$)$_4$CH$_3$ (Compound A-4). In another particular embodiment of formula (I'), R$^1$ is —CH$_2$OC(O)—(CH$_2$)$_{10}$CH$_3$ (Compound A-7). Compounds A-4 and A-7 are depicted below:

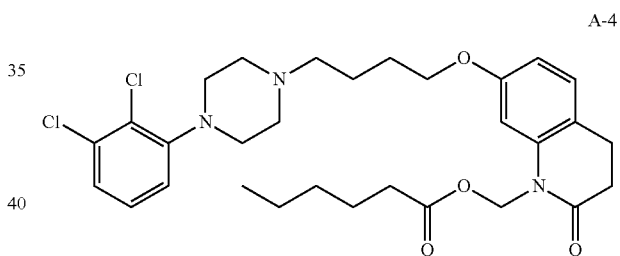

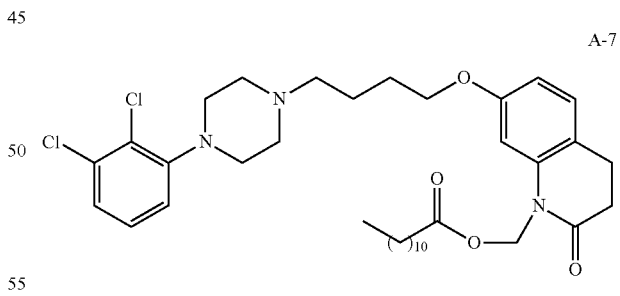

In another embodiment, the antipsychotic drug of the pharmaceutical composition is olanzapine. The olanzapine drug substance can comprise, consist essentially of, or consist of olanzapine (in a crystalline, non-crystalline or amorphous form), an olanzapine salt, an olanzapine solvate (including for example ethanolates and hydrates), or other olanzapine polymorphs. A preferred olanzapine salt is olanzapine pamoate. The antipsychotic drug can also be an olznapine prodrug.

The olanzapine drug substance can also include olanzapine prodrugs of Formula (III), or (IV):

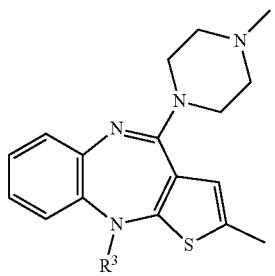

(III)

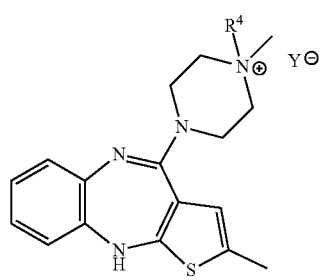

(IV)

wherein

R³ is —CH₂OC(O)R¹, —CH₂OC(O)OR¹, —CH₂OC(O)N(R¹)₂ or —C(O)R¹;

R⁴ is —CH₂OC(O)R¹, —CH₂OC(O)OR¹, —CH₂OC(O)N(R¹)₂ or —C(O)R¹;

wherein each R¹ is independently selected from the group consisting of hydrogen, substituted or unsubstituted aliphatic, and substituted or unsubstituted aryl; and wherein Y⁻ is a pharmaceutically acceptable counterion.

Suitable counterions include, e.g., chloride, bromide, iodide, sulfate, phosphate, acetate, benzoate, tartrate, citrate, propionate, gluconate, lactate, maleate, fumarate, camsylate, glucepate, mesylate, napsylate, pamoate, conjugate bases of organic carboxylic acids, and the like.

In another embodiment, the antipsychotic drug of the pharmaceutical compositions is lurasidone. Lurasidone is an atypical antipsychotic that is useful for the treatment of a variety of psychiatric disorders, including schizophrenia and bipolar disorder. This compound is described in, e.g., U.S. Pat. No. 5,532,372, which is incorporated herein by reference. Lurasidone is the generic name of the compound (3aR,4S,7R,7aS)-2-[((1R,2R)-2-{[4-(1,2-benzisothiazol-3-yl)-piperazin-1-yl]methyl}cyclohexyl)methyl]hexahydro-1H-4,7-methanisoindol-1,3-dione:

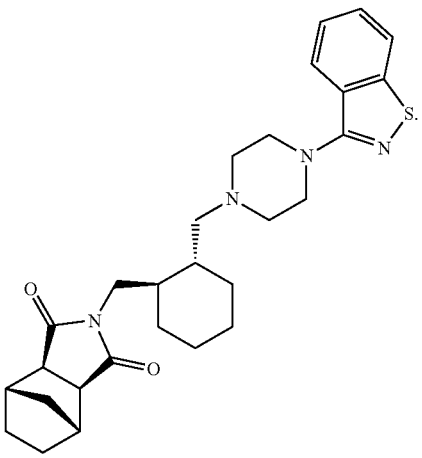

(V)

The lurasidone drug substance can comprise, consist essentially of, or consist of lurasidone free base (in a crystalline, non-crystalline or amorphous form), a lurasidone salt, a lurasidone solvate (including for example ethanolates and hydrates), or other lurasidone polymorphs. The lurasidone drug substance can also include lurasidone prodrugs.

Accordingly, aripiprazole, or olanzapine, or a compound of formula I, II, III, IV, or V can be referred to as an "antipsychotic agent" or "water-insoluble antipsychotic agent."

An "aliphatic group" or "aliphatic" is non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted.

An aliphatic group, when used as a linker, preferably contains between about 1 and about 24 atoms, more preferably between about 4 to about 24 atoms, more preferably between about 4 to about 12 atoms, more typically between about 4 and about 8 atoms. An aliphatic group, when used as a substituent, preferably contains between about 1 and about 30 atoms, more preferably between about 4 to about 19 atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl groups described herein.

In certain embodiments, the aliphatic groups of the present invention are alkyl chains containing from 5 to 11 carbon atoms. In other embodiments, the aliphatic groups are alkyl chains containing from 15 to 19 carbon atoms.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. In an embodiment, aryl is unsubstituted or independently substituted one or more times with halogen, $C_{1-6}$ alkyl, or $O—C_{1-6}$ alkyl.

The term "heteroaryl" embraces unsaturated heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkylsulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The term "compound" is defined herein to include pharmaceutically acceptable salts, solvates, hydrates, polymorphs, enantiomers, diastereoisomers, racemates and the like of the compounds having a formula as set forth herein.

Methods of Treatment

The pharmaceutical compositions provided herein can be used for treatment of a variety of disorders in a subject in need thereof. For example, the disclosed compositions may be used to treat conditions selected from: disorders such as cerebral deficit subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, cerebral deficits secondary to prolonged status epilepticus, migraine (including migraine headache), urinary incontinence, substance tolerance, substance withdrawal (including, substances such as opiates, nicotine, tobacco products, alcohol, benzodiazepines, cocaine, sedatives, hypnotics, etc.), psychosis, schizophrenia, anxiety (including generalized anxiety disorder, panic disorder, social phobia, obsessive compulsive disorder, and post-traumatic stress disorder (PTSD)), attention deficit disorder (ADD), attention deficit hyperactivity disorder (ADHD), mood disorders (including depression, mania, bipolar disorders), circadian rhythm disorders (including jet lag and shift work), trigeminal neuralgia, hearing loss, tinnitus, macular degeneration of the eye, emesis, brain edema, pain (including acute and chronic pain states, severe pain, intractable pain, neuropathic pain, inflammatory pain, and post-traumatic pain), tardive dyskinesia, sleep disorders (including narcolepsy), attention deficit/hyperactivity disorder, and conduct disorder.

In another embodiment, the present invention provides a method of treating cardiac and cardiovascular disorders such as angina, arrhythmia, and hypertension, in a patient in need thereof. The method comprises administering to the subject a therapeutically effective amount of a composition of the invention or a pharmaceutically acceptable salt thereof.

The invention further relates to the treatment of fever, diabetes, allergy, asthma, infection, inflammation, and ulcers in a patient in need thereof, comprising administering to the subject a therapeutically effective amount of a composition of the invention or a pharmaceutically acceptable salt thereof.

The invention further relates to the treatment of sleep modulation comprising administration of a composition of the invention. Sleep modulation includes decreasing the time to sleep onset, increasing the average sleep bout length, and increasing the maximum sleep bout length.

In a particular embodiment, the pharmaceutical compositions described herein can be used to treat anxiety, depression, bipolar disorder, autism-related irritability, and psychotic conditions including acute mania, schizophrenia and schizophreniform diseases in a subject.

The term "treated," "treating" or "treatment" includes the diminishment or alleviation of at least one symptom associated with psychosis or a related CNS disorder. The term "treated," "treating" or "treatment" as used in reference to a disease or condition shall mean to intervene in such disease or condition so as to prevent or slow the development of, prevent or slow the progression of, halt the progression of, or eliminate the disease or condition.

As used herein, the term "modulating" or "modulate" refers to an effect of altering a biological activity, especially a biological activity associated with an injection site reaction.

The term "subject" is intended to include animals, which are capable of suffering from or afflicted with dementia associated with psychosis or a related CNS disorder, including, without limitation, psychotic conditions including acute mania, schizophrenia and schizophreniform disorders, bipolar disorder, anxiety and depression. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from any of the diseases described herein.

The term "about" or "approximately" usually means within 20%, more preferably within 10%, and most preferably still within 5% of a given value or range. Alternatively, especially in biological systems, the term "about" means within about a log (i.e., an order of magnitude), preferably within a factor of two of a given value.

In one embodiment, a therapeutically effective amount of the agent is given to a subject using the pharmaceutical compositions provided herein. The term "therapeutically effective amount" is further meant to define an amount resulting in the improvement of any parameters or clinical symptoms. The actual dose may vary with each patient and does not necessarily indicate a total elimination of all disease symptoms. In the case of antipsychotics, the management of exacerbations and maintenance of remission of psychiatric symptoms are main goals of therapy, and selection of the appropriate drug and dosage in a particular disease balances these goals with the minimization of adverse events attributable to the drug.

A therapeutically effective amount of the compound used in the treatment described herein can be readily determined by the attending diagnostician, as one skilled in the art, by the use of conventional techniques and by observing results obtained under analogous circumstances. In determining the therapeutically effective dose, a number of factors are considered by the attending diagnostician, including, but not limited to: the species of mammal; its size, age, and general health; the specific disease involved; the degree of or involvement or the severity of the disease; the response of the individual patient; the particular compound administered; the mode of administration; the bioavailability characteristic of the preparation administered; the dose regimen selected; the use of concomitant medication; and other relevant circumstances.

Preferred suitable dosages for the compounds used in the treatment described herein are on the order of about 1 mg to about 600 mg, preferably about 3, 5, 10, 15, 20, 25, 30, 35, 40, 45, 50, 55, 60, 65, 70, 75, 80, 90, 95, 100, 120, 140, 160, 180, 200, 220, 240, 260, 280, 300, 320, 340, 360, 380, 400, 420, 440, 460, 480, 500, 520, 540, 560, 580 to about 600 mgs total of active agent. Dosing schedules may be adjusted to provide the optimal therapeutic response. For example, administration can be one to three times daily for a time course of one day to several days, weeks, months, and even years, and may even be for the life of the patient. Practically speaking, a unit dose of any given composition used in the treatment described herein can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth. Unit dose preparations provided herein can contain aripiprazole, a compound of Formula I or a compound of Formula II in the range of about 20 to about 900, e.g., 60 to about 800, mgs (aripiprazole base equivalents). Unit dose preparations provided herein can contain olanzapine, a compound of Formula III, or a compound of Formula IV in the range of 40 to about 500 mgs (olanzapine base equivalents). Unit dose preparations provided herein can contain a compound of Formula V in the range of 160 to about 1000 mgs (lurasidone base equivalents).

Preferred amounts according to the selected mode of administration are able to be determined by one skilled in the art. Pharmaceutical compositions can be manufactured utilizing techniques known in the art. Typically the therapeutically effective amount of the compound will be admixed with a pharmaceutically acceptable carrier.

EXEMPLIFICATION OF THE INVENTION

The invention is further illustrated by the following examples. The examples should not be construed as further limiting.

EXAMPLE I

Formulation Optimization of Antipsychotic Drug Product

This study describes the formulation development of the Compound A-7 drug product for use in further studies. Development was focused on improving the wettability and redispersibility characteristics of the injection vehicle, with the ultimate intent of increasing the physical stability of the suspension. The optimization experiments identified a formulation comprising Compound A-7 recrystallized bulk drug substance (256 mg/mL) suspended in an 10 mM phosphate buffer injection vehicle containing sorbitan laurate (0.5 wt %), polysorbate 20 (0.2 wt %), and sodium chloride, (0.8 wt %).

While the early clinical formulation was deemed acceptable for short-term study, there was a desire to improve the physical properties of the drug product suspension (namely ease of manufacturing, and resuspendability with increased drug loads) for long term use. Optimization of these properties would also improve the likelihood of success in a prefilled syringe, in the event such a system becomes a desired container closure configuration. The strategy for formulation development consisted of a two-tiered approach designed to screen a wide array of injection vehicles and identify promising candidates for further optimization. The first round of experiments assessed wettability characteristics, specifically free energy of immersion and spreading coefficient, of various vehicles with Compound A-7 Immersion of a solid in a liquid (wetting) begins with displacement of the solid-air interface with a solid-liquid interface. The immersional free energy in this solid/liquid/air system describes how thermodynamically favorable (or unfavorable) exchange of these interfaces is. The spreading coefficient predicts whether this exchange will occur spontaneously, or will require additional energy input. Thus, these parameters were selected for study since they would be good indicators of the favorability of the vehicles to wet the hydrophobic drug substance, and the relative difficulty of doing so. The excipients screened were primarily limited to materials that have been used in approved drug products (although not necessarily limited to parenteral routes of administration) with acceptable safety profiles [Rowe, Raymond C., Paul J. Sheskey, and Paul J Weller. Handbook of Pharmaceutical Excipients, 4th Ed. New York, Pharmaceutical Press. 2003]. The excipients screened represent a number of functionalities in the formulation of stable suspensions, including suspending agents, surfactants/wetting agents, viscosity modifiers, co-solvents and flocculants. The injection vehicles that were found to have favorable wetting characteristics with Compound A-7 were then advanced to the second tier of experiments.

Description of Excipients Utilized

| MATERIAL | ABBREVIATION | TRADE NAME(S) | MANUFACTURER |
|---|---|---|---|
| Sodium carboxymethyl cellulose | CMC | N/A | Spectrum |
| Poloxamer 188 | P188 | Pluronic ® F68 | Spectrum |
| Polyvinylpyrrolidone K15 | PVP, Povidone | Plasdone ® K-15 | |
| Polyvinylpyrrolidone K30 | N/A | Plasdone ® K-30 | Sigma USP |
| Polyethylene glycol 3350 | PEG3350 | N/A | Sigma |
| Polyethylene glycol 300 | PEG 300 | N/A | Emerald Bio |
| Polysorbate 20 | PS 20 | Tween ® 20 | Sigma |
| Polysorbate 80 | PS 80 | Tween ® 80 | EMD |
| Sorbitan monolaurate | SML | Span ® 20, Montane ® 20 | Sigma-Aldrich |
| Sorbitan monopalmitate | SMP | Span ® 40 | Aldrich |
| Sodium chloride | NaCl | N/A | EMD |
| Mannitol | N/A | N/A | Merck |
| Dextrose | N/A | N/A | Sigma-Aldrich |
| Monobasic sodium phosphate (dihydrate) | N/A | N/A | EMD |
| Dibasic sodium phosphate (anhydrous) | N/A | N/A | J. T. Baker |
| Phosphate buffered saline tablets* | PBS | N/A | Sigma |
| Docusate sodium | N/A | N/A | Sigma |

*One tablet dissolved in 200 mL of deionized water yields 0.01M phosphate buffer, 0.0027M potassium chloride and 0.137M sodium chloride, pH 7.4, at 25° C.

5.2 Methods 5.2.2 Injection Vehicle Formulation

Injection vehicles were made by weighing the appropriate mass of excipient into a metered volume of water for injection (WFI) to give the desired weight percentage by volume. Since the excipient quantities were typically low (<1%), the volume change from addition was considered negligible. In the cases where multiple surfactants were added, the more water-soluble surfactant was added first to aid in dispersion of the less soluble surfactant. The vehicle formulations were then stirred with a magnetic stir plate until all solids were dissolved and the vehicle appeared visually homogeneous.

5.2.3 Compound A-7 Drug Product Compounding

The suspension was formed by adding recrystallized Compound A-7 to the formulated injection vehicle with mixing to achieve the target drug concentration. At the bench scale, this was done on a vial-by-vial basis. The appropriate mass of Compound A-7 was weighed into a 5 mL siliconized glass vial and the appropriate volume of vehicle was added to achieve the desired suspension concentration. The vial was then stoppered/sealed and mixed by alternating between a vortex mixer and a 60 second sonication bath. This procedure was typically repeated 7 times (total of 7 minutes). After compounding, the absence of aggregates or unincorporated powder was visually confirmed.

5.2.5 Wettability Characterization

A surface energy measurement methodology was developed that would allow for facile screening of formulation candidates with minimal use of drug substance. These experiments utilize the surface tension of the injection vehicle and surface energy of the solid to predict the immersional free energy and spreading coefficient between the liquid and the solid.

5.2.6 Liquid Surface Tension Analysis

A force-balance tensiometer (Attension Sigma® 701) with a platinum Wilhelmy plate was used to measure the surface energy (tension) of the vehicle of interest. This was done using a 30 mL sample of the vehicle of interest and taking 8 individual surface tension measurements. The first 3 measurements were discarded as being non-representative of equilibrium conditions, and the remaining measurements were averaged to give the surface tension value. The vehicle sample contained a small (approx. 10 mm) stir bar and the magnetic stir plate in the tensiometer was turned to the lowest setting to allow for mixing without significant disruption of the measurement. All measurements were taken at ambient conditions. To then obtain the polar and non-polar (dispersive) components of the surface tension, a polytetrafluoroethylene (PTFE) contact angle standard (Rame-Hart) was affixed to the tensiometer and the dynamic contact angle was measured. Since the desired measurement was the static contact angle, a very slow measurement speed was used (0.001 m/min) which allowed for approximation of the $t \to \infty$ (infinite time) condition. This was done using a 30 mL sample of the vehicle of interest and taking the average of 3 individual contact angle measurements. The vehicle sample contained a small (approx. 10 mm) stir bar and the magnetic stir plate in the tensiometer was turned to the lowest setting to allow for mixing without significant disruption of the measurement. All measurements were taken at ambient conditions.

With the total surface tension of the liquid, and the contact angle of the liquid on a non-polar surface with known surface energy attributes, the polar and dispersive components of the surface tension were calculated.

5.2.7 Solid Surface Energy Analysis

A force balance tensiometer (Kruss K100) with a Washburn-type powder measurement apparatus (Kruss FL12) was used to obtain the polar and dispersive surface energy components of the Compound A-7 sample. This was done by using probe liquids with precisely characterized surface tensions (diiodomethane and ethylene glycol) and measuring the rate at which the probe liquids wick up into a packed, 125 mg bed of the powder by capillary action. The contact angle experiments were performed on the samples according to the Washburn method for the determination of contact angles for liquids wetting porous materials. The contact angle data with diiodomethane and ethylene glycol were used along with the Fowkes theory to obtain the surface energy data.

5.2.8 Redispersibility/Settled Bed Height Characterization

The redispersibility of the drug products were assessed by creating low concentration suspensions and comparing the relative height of the settled beds. Higher settled bed heights are indicative of flocculated, or loosely aggregated, particles. These suspensions settle faster initially, but their loosely aggregated state allows for easier redispersion and better physical stability as the particles cannot pack as tightly as fully dispersed suspensions.

The experiments were made using a concentration of 220±22 mg of Compound A-7 in 3 mL of the vehicle of interest (73.3 mg/mL). The lower concentration was used to allow for easier rank ordering of settled bed heights as well as for material conservation. A key assumption was that this rank ordering would be the same at full concentration. This suspension was compounded in a 5 mL vial, drawn into a 3 mL BD plastic syringe using an 18G needle, capped, placed upright and allowed to settle. Early experiments showed that suspensions were fully settled after approximately 10 hours, and that subsequent time did not result in any discernable amount of further bed packing. As such, all suspensions tested were allowed to settle for a minimum of 16 h and a maximum of 48 h prior to being characterized.

Settled bed heights were assessed by qualitatively recording the height of the undisturbed bed and total height of the liquid using the graduations on the 3 mL syringes. Formulations that looked promising (highest bed heights) at lower concentrations were also screened at full concentration (810 mg in 3 mL—equivalent to 270 mg per mL vehicle) to qualitatively assess redispersibility.

6.0 Results and Discussion

TABLE 1

Free Energy of Immersion and Spreading Coefficient of Compound A-7 in Various Formulations

| FORMULATION | FREE ENERGY OF IMMERSION (mN/m) | SPREADING COEFFICIENT (mN/m) |
|---|---|---|
| 2% CMC - 0.2% PS 20 | −30 | −0.6 |
| 2% PEG3350 - 0.2% PS 20 - 2% Eth | −30 | −3.8 |
| 0.2% Docusate Sodium | −30 | 1.2 |
| 4% PEG3350 - 0.8% SML - 0.5% PS 20 | −29 | 2.6 |
| 0.8% SML - 0.5% PS 20 | −29 | 2.3 |
| 4% PEG 3350 - 0.2% PS 20 | −29 | −6.1 |
| 2% PEG 3350 - 0.2% PS 20 | −28 | −5.6 |
| 2% PEG3350 - 0.2% PS 20 - 1% Eth | −29 | −6.1 |
| 2% CMC - 0.2% PS 20 - PBS - (SAD) | −28 | −5.5 |
| 6% PEG3350 - 0.2% PS 20 | −28 | −6.6 |
| 2% CMC - 0.2% PS 80 | −28 | −6.7 |
| 4% PEG 3350 - 0.5% PS 20 | −27 | −6.5 |
| 1% CMC - 0.8% SML - 0.5% PS 20 | −27 | 0.8 |
| 2% CMC - 0.5% PS 20 | −26 | −7.3 |
| 40% PEG 300 | −23 | −19.6 |
| 4% PEG 3350 | −23 | −37.5 |
| 2% PEG 3350 | −22 | −34.8 |
| 2% CMC - 0.2% Poloxamer 188 | −21 | −25.2 |
| 0.8% SMP - 0.5% PS 20 | −19 | −13.1 |
| 1% CMC - 0.8% SMP - 0.5% PS 20 | −17 | −14.6 |
| 2% PVP K30 | −12 | −47.5 |
| 2% PVP K15 | −8 | −60.0 |
| Water | 10 | −83.3 |

As shown in Table 1, the free energy of immersion for all formulations tested against all recrystallized Compound A-7 samples was found to be negative, with the exception of pure water. Free energy of immersion describes the energy gained or lost when displacing the air-solid interface with a liquid-solid interface. If the sign is negative, the liquid-solid interface (created by wetting) is more energetically favorable, and if the sign is positive, the air-solid interface is more energetically favorable. Examination of the data shows that formulations containing sorbitan laurate, polysorbate 20 and polysorbate 80 are the most favored (most negative free energy of immersion value).

While all vehicle formulations tested have thermodynamically favorable immersional free energies, the data in Table 1 illustrate that formulations are differentiated by their spreading coefficients. The value of spreading coefficient indicates whether the replacement of the air-solid interface by the liquid-solid interface will occur spontaneously. The results show that vehicle formulations containing docusate sodium and sorbitan laurate/polysorbate 20 combinations have positive spreading coefficients, which means they will replace the solid-air interface with the solid-liquid interface without the addition of work (i.e. spreading occurs spontaneously). A positive spreading coefficient is desirable because of an increased likelihood of complete deaggregation/wetting of the powder during suspension compounding leading to an overall ease of processing.

In summary, while analysis of the wetting data show that practically all formulations are predicted to wet, with the most favored formulations containing a surfactant such as polysorbate 20, polysorbate 80, sorbitan laurate or docusate sodium, review of the spreading coefficient data identified formulations that are spontaneously wetting. The latter has positive implications for processing ease and robustness. As such, these materials were selected as the area of focus in the subsequent redispersibility studies discussed in Section 6.4.

6.4 Redispersibility/Settled Bed Height

The results from the settled bed height assessments are presented in FIG. 1. The data indicate that formulations containing sorbitan laurate and polysorbate 20 have significantly higher settled bed heights than formulations without sorbitan laurate, regardless of the presence of additional polymers (CMC, PEG 3350) or salts (phosphate buffer, saline). Additionally, the flocculation induced is unique to sorbitan laurate/polysorbate 20, as evidenced by comparison to formulations containing sorbitan monopalmitate, docusate sodium, or polysorbate 20 alone.

Experiments were also performed to assess whether the induced flocculation could be uniquely attributed to the presence of sorbitan laurate, or whether it was the result of an increase in total surfactant load. Suspensions were made with an equivalent mass load of polysorbate 20 and polysorbate 80 (1.3 wt %) and an equivalent molar content load of polysorbate 20 (3.1 wt %) to the total surfactant load of a 0.5% sorbitan laurate/0.2% polysorbate 20 suspension. The suspensions with increased polysorbate 20 were found to have similar settled bed heights to 0.2 wt % polysorbate formulations, showing the flocculation phenomenon to be uniquely attributed to the additional influence of sorbitan laurate.

Compared with other formulations, the sorbitan laurate/polysorbate 20 formulations resuspend more easily after settling, and as such these suspensions were made at the full concentration of 21 wt %. At full concentration settled bed heights could not be measured as the flocculated bed filled the entirety of the syringe volume. Qualitative assessment of redispersibility showed the settled bed to be easily disrupted with moderate hand shaking of the vials.

In an effort to optimize the ratio between sorbitan laurate and polysorbate 20, suspensions were made in 0.2% polysorbate 20 with phosphate buffered saline and the amount of sorbitan laurate varied between 0.2% and 0.6% (representing sorbitan laurate: polysorbate 20 ratios from 1:1 to 3:1). The results are shown in FIG. 2. The settled bed height increases to a maximum at a 2:1 ratio, after which, increasing sorbitan laurate concentration has no further effect on bed height. In order to select a formulation in a robust formulation space, the 10 mM phosphate buffer injection vehicle containing sorbitan laurate (0.5 wt %), polysorbate 20 (0.2 wt %), and sodium chloride, (0.8 wt %) was selected as the lead candidate and advanced into further studies.

7.0 Example I Conclusion

The optimized Compound A-7 drug product (Compound A-7 recrystallized bulk drug substance suspended in an 10 mM phosphate buffer injection vehicle containing sorbitan laurate (0.5 wt %), polysorbate 20 (0.2 wt %), and sodium chloride, (0.8 wt %)) was found to meet all target criteria and exhibits improved physical attributes (redispersibility, ease of wetting) when compared to the Compound A-7 recrystallized bulk drug substance (21 wt %) suspended in an 5 mM phosphate buffer injection vehicle containing sodium carboxymethyl cellulose (2 wt %), polysorbate 20 (0.2 wt %), and sodium chloride, (0.7 wt %). The optimized formulation is physically and chemically stable when compounded as a 21 wt % suspension (approximately 221 mg/mL) and as a 25.6 wt % suspension (approximately 270 mg/mL).

EXAMPLE II

Evaluation of Performance of Compound A-7 Suspensions Containing Varied Amounts of Sorbitan Laurate and Polysorbate 20: Optimization of Excipient Concentrations and Sorbitan Laurate to Polysorbate 20 Ratio The objective of this study was to evaluate formulation performance of Compound A-7 suspensions containing varied amounts and ratios of sorbitan laurate and polysorbate 20 in an effort to establish a robust region for the drug product which meets all target product attributes.

An array of vehicle formulations were evaluated and a lead drug product candidate consisting of Compound A-7 bulk recrystallized drug substance (25.6 wt %) suspended in an 10 mM phosphate buffer injection vehicle containing sorbitan laurate (0.5 wt %), polysorbate 20 (0.2 wt %), and sodium chloride, (0.8 wt %) was identified.

During development, settled bed height and qualitative ease of re-suspension were assessed and utilized to identify a lead formulation. Increases in these properties are associated with flocculation, a common mechanism used to increase physical stability of pharmaceutical suspensions [Akers, M., Fites, A. and Robison, R. Formulation Design and Development of Parenteral Suspensions. Journal of Parenteral Science and Technology Vol. 41, No. 3 (pp. 88-96), 1987; and Lieberman, Herbert A., Martin M. Reiger and Gilbert S. Banker. Pharmaceutical Dosage Forms: Disperse Systems Volume 2. (pp 18-22, 285-301) 2nd Ed. New York: Marcel Dekker, 1996.]. Flocculation refers to the formation of loose aggregates held together by interparticular forces. The sediment layer in a flocculated suspension is loosely packed and more easily redispersed compared to non-flocculated formulations in which a dense cake can form. Further experiments to quantify flocculation and formulation performance with vehicles containing varied amounts of sorbitan laurate and polysorbate 20 were designed, executed and analyzed. These follow-on experiments are detailed below.

5.2 Methods

TABLE 2

Amounts and Ratios of Surfactanct Components in Vehicles Examined

| Vehicle | Sorbitan Monolaurate (g/100 mL) | Polysorbate 20 (g/100 mL) | Nominal Mass Ratio SML/PS20 |
|---|---|---|---|
| A | 0 | 0.1 | 0 |
| B | 0 | 0.2 | 0 |
| C | 0 | 0.5 | 0 |
| D | 0 | 0.8 | 0 |
| E | 0.5 | 0.1 | 5 |
| F | 0.5 | 0.2 | 2.5 |
| G | 0.5 | 0.5 | 1 |
| H | 0.5 | 0.8 | 0.625 |
| I | 1 | 0.2 | 5 |
| J | 1 | 0.5 | 0.625 |
| K | 1 | 0.8 | 1.25 |

5.2.2 Compound A-7 Drug Product Compounding

Compound A-7 suspensions (265 mg/mL±10%) were prepared by adding 3 mL of injection vehicles listed in Table 1 to 1032 mg of Compound A-7 bulk recrystallized drug substance in a 5 ml siliconized glass vial. Each vial was sealed with a rubber stopper and an aluminum seal. Suspensions vials were roughly mixed by vortexing and tapping to facilitate initial wetting of the solids. Each vial was then sonicated in a bath sonicator for 10 minutes, with ~5 second vortexing every minute.

5.2.4 Suspension particle size measurement

Particle size distribution of formulated suspension was measured on a Horiba LA910 laser diffraction particle size analyzer equipped with a flow through sample cell using 0.1% polysorbate 20 solution as measurement media. Suspension samples were prepared for measurement by re-suspending the vial containing drug product and then adding 0.1 mL of suspension to 10 mL of 0.1% polysorbate 20 solution. A sample was then added dropwise to the Horiba flow-through sample cell until dispersion transmittance drops below 95%. The particle size metrics examined were volume diameter where 10%, 50%, and 90% of the particle size distribution was smaller than that diameter (Dv[10], Dv[50], and Dv[90]).

5.2.5 Sediment Height Measurements

Sediment height was measured after allowing vials sit undisturbed for at least 24 hours. A close up picture of all vials together was taken using a digital camera, with lighting such that the sediment layer could clearly be seen in the picture. The distance from the bottom of the vial to the surface of liquid layer and to the surface of sediment layer was measured from each picture. The ratio of line lengths from each vial were calculated and reported as sediment height in percentage, as shown in FIG. 3. A sediment height of 100% would indicate that no sediment layer is visible.

Injectability

Injectability was conducted to assess the ability of the suspension to be passed through a 20 G or greater needle without clogging, with minimal resistance applied through use of a mesh screen.

5.2.7 Re-suspension Time

Re-suspension time was measured using a Burrel wrist action shaker. Vials were shaken at max amplitude on the wrist action shaker in an inverted orientation (cap down) for 5 second intervals. Re-suspension time was recorded when no visual clumps or caked material was observed at the bottom of the vial.

5.2.8 Microscopy

For microscopic analysis, 5 μL of suspension was placed on a glass slide and then diluted with 20 μL of same vehicle used to make the suspension. The sample was covered with a coverslip and examined at 10× magnification using an Olympus BX60 microscope. Pictures were taken using an Axio-Cam MRc camera.

5.3 Design of Experiment

Using JMP 9 software, a central composite design of experiment (DOE) was initiated with the factors of SML (0-1% w/v) and polysorbate 20 (0.1-0.8% w/v) concentrations. Previous experiments showed that at least 0.1% polysorbate 20 is required to adequately wet a 25.6 wt % solids load of Compound A-7 bulk recrystallized drug substance therefore the lower limit of 0.1% is deemed to be the lowest possible level of the surfactant required to achieve wetting of the highly hydrophobic Compound A-7 crystals. The final DOE factors are summarized in Table 3.

TABLE 3

Design of Experiment Factors to look at varied concentrations of SML and polysorbate 20

| Sample | SML % | Polysorbate 20% | SML/Polysorbate 20 Ratio |
|---|---|---|---|
| 1 | 0 | 0.8 | 0 |
| 2 | 0 | 0.5 | 0 |
| 3 | 1 | 0.8 | 1.25 |
| 4 | 0 | 0.2 | 0 |

TABLE 3-continued

Design of Experiment Factors to look at varied concentrations of SML and polysorbate 20

| Sample | SML % | Polysorbate 20% | SML/Polysorbate 20 Ratio |
|---|---|---|---|
| 5 | 0.5 | 0.5 | 1 |
| 6 | 0.5 | 0.5 | 1 |
| 7 | 0.5 | 0.2 | 2.5 |
| 8 | 0.5 | 0.5 | 1 |
| 9 | 1 | 0.5 | 2 |
| 10 | 0.5 | 0.8 | 0.625 |
| 11 | 1 | 0.2 | 5 |
| 12 | 0.5 | 0.1 | 5 |
| 13 | 0 | 0.1 | 0 |

The measured responses were: sediment height, re-suspension time, particle size distribution (Dv[10], Dv[50], and Dv[90]), and injectability. Microscopy was also performed on each sample.

6.0 Results and Discussion 6.1 Microscopy and Visual Observations

Microscopy of three suspensions made with vehicle containing 0.2% polysorbate 20 and increasing amounts of SML are shown in FIG. 4. It is visually clear that flocculation is occurring as SML content in the vehicle increases. Measured suspension PSD, listed below each image in units of microns, increases relative to the PSD method variability (approx. 2-3 microns) with increased degree of flocculation. This observation supports using suspension particle size measurements to quantify flocculation in that the method preparation maintains flocculation induced by the vehicle. The methodologies established by this type of pilot experiment facilitated the initiation of DOE experimentation.

6.2 DOE Responses

The desired Compound A-7 drug product formulation attributes include maximum ease of resuspension and injectability, the ability of the suspension to be passed through a 20 or greater gauge needle without clogging with minimal resistance applied through use of a mesh screen. Re-suspension time, sediment height, and suspension particle size distribution are all physical measurements of the formulated suspension used to assess ease of re-suspension. These responses are related since particle size of the suspension can be a measure of flocculation, which increases the sediment height and decreases re-suspension time. A summary of all responses measured is listed in Table 4.

6.3 Resuspension Time, Sediment Height and Particle Size Responses

A photograph of vials containing suspension after sedimentation with sediment height calculations is shown in FIG. 5. In the two panels of FIG. 6 are plotted the observed re-suspension time vs. Dv[10] and Dv[50] values for each suspension. The measured re-suspension time and particle size metrics exhibit an inverse relationship for the suspensions with smaller measured particle size (below 11 and 32 microns for Dv[10] and Dv[50], respectively). Larger measured suspension particle sizes, likely caused by flocculation, facilitate faster re-suspension than smaller ones.

Trends of particle size (Dv[10] and Dv[50]) with vehicle composition were modeled resulting in surface plots (not shown). As SML concentration increased and polysorbate 20 concentration decreased, suspension particle size reflected by Dv[10] and Dv[50] increased. The smallest Dv[10] and Dv[50] were measured from suspensions containing polysorbate 20 with no addition of SML. For suspensions containing 0.1% polysorbate 20, Dv[10] and Dv[50] increased rapidly with increasing SML. These data are consistent with the understanding that SML is required for the flocculation of the drug product, which results in an increase in apparent suspension particle size and therefore a decrease in re-suspension time.

6.5 Formulation Space

The desired Compound A-7 drug product is comprised of an injection vehicle which facilitates re-suspension with optimal ease without decreasing injectability of the suspension to an unacceptable level. Increases in measured suspension particle size parameters directly correlate to ease of re-suspension but inversely correlate with injectability. Hence, a formulation with high SML wt % and low polysorbate 20 wt % would have the shortest re-suspension time but would also have the worst injectability. The optimal vehicle composition is one where a balance between ease of resuspension and injectability is achieved through a balance in the amounts and ratios of SML and polysorbate 20. The profiles in FIG. 6 show that when the measured suspension Dv[10] is greater than 11 µm or the measured suspension Dv[50] is greater than 32 microns, optimal re-suspension time is achieved. The values of 11 and 32 microns for Dv[10] and Dv[50], respectively, were used to set limits within the modeled data in order to define the acceptable formulation space.

Previous experiments showed that at least 0.1% polysorbate 20 is required to adequately wet a 25.6 wt % 256 mg/mL±10% concentration of Compound A-7 bulk recrys-

TABLE 4

| | SML % | Polysorbate 20% | Sediment Height | Injectable (20-25 gauge needle) | Dv[10] (µm) | Dv[50] (µm) | Dv[90] (µm) | Resuspension Time (s) |
|---|---|---|---|---|---|---|---|---|
| 1 | 0 | 0.8 | 39% | Yes | 8.7 | 25.2 | 53.8 | 15 |
| 2 | 0 | 0.5 | 34% | Yes | 8.6 | 24.5 | 51.2 | 20 |
| 3 | 1 | 0.8 | 68% | Yes | 10.9 | 28.3 | 57 | 10 |
| 4 | 0 | 0.2 | 34% | Yes | 8.5 | 24 | 51.3 | 20 |
| 5 | 0.5 | 0.5 | 50% | Yes | 10.3 | 29.4 | 62.1 | 10 |
| 6 | 0.5 | 0.5 | 48% | Yes | 11 | 31.9 | 65.9 | 5 |
| 7 | 0.5 | 0.2 | 80% | Yes | 14.4 | 33.6 | 61.6 | 5 |
| 8 | 0.5 | 0.5 | 48% | Yes | 10.4 | 30.4 | 62.7 | 10 |
| 9 | 1 | 0.5 | 73% | No | 15.9 | 36.3 | 66.2 | 5 |
| 10 | 0.5 | 0.8 | 34% | Yes | 8.7 | 24.8 | 55.8 | 20 |
| 11 | 1 | 0.2 | 84% | No | 20.1 | 41 | 70.8 | 5 |
| 12 | 0.5 | 0.1 | 88% | No | 8.7 | 24 | 51.8 | 5 |
| 13 | 0 | 0.1 | 38% | Yes | 14.5 | 34.7 | 66.7 | 20 | tallized drug substance. In order to account for small changes in Compound A-7 bulk recrystallized drug substance surface area as well as potential loss of polysorbate 20 on stability, at least 0.2% polysorbate 20 is recommended for the vehicle composition. At this polysorbate 20 concentration, 0.5% SML concentration minimizes excipient levels while still maximizing re-suspendability with acceptable injectability. This surfactant combination is indicated in FIG. 7 by the intersection of the horizontal and vertical lines.

7.0 Example II Conclusion

Formulation performance of Compound A-7 suspensions containing varying amounts and ratios of SML and polysorbate 20 were evaluated and a robust region for the drug product which meets all target product attributes was established. Compound A-7 suspension drug product formulated in an injection vehicle containing 0.5% SML and 0.2% polysorbate 20 is within the robust region of the formulation space, as derived from analysis of the DOE executed. This vehicle composition minimizes excipient levels while co-optimizing resuspendabilty and acceptable injectability.

EXAMPLE III

Injection Site Reaction Modulation

Subcutaneous Injection Site Reaction Model Protocol and Data

The following experimental protocol and data relate to the effect of vehicle on the ISRs caused by subcutaneous (SC) administration of aripiprazole (ARP) free base to rats.

Description of Experimental Design:

Overview of experimental design: There were 7 groups (n=6) in this study evaluating ISRs caused by ARP formulated in 7 different vehicles; a standard vehicle was used as the control to which other compositions of vehicle were compared. All groups received a single SC injection of ARP at a dose of 30 mg in a 1 mL dose volume. A 21-gauge, 1 inch needle attached to a 1 cc syringe was used to administer the drug. Ten days following injection with ARP, animals were euthanized by $CO_2$ asphyxiation, and the ISR was excised and weighed. Weights of the ISRs were plotted against dose administered.

Materials and Methods:
  Aripiprazole (ARP) dose 30 mgs;
  Control Vehicle: 0.1% Polysorbate 20 (Tween® 20)/, 3% CMC, 0.9% NaCl in water
    Vehicle A: 0.2% Polysorbate 20 (Tween® 20)/0.5% sorbitan laurate (Span® 20) in PBS buffer (10 mM, pH ~7)
    Vehicle F: 0.2% Polysorbate 40 (Tween® 40)/0.5% sorbitan monopalmitate (Span® 40) in PBS buffer (10 mM, pH ~7)
    RELPREVV® Vehicle: CMC, mannitol, polysorbate 80, sodium hydroxide and/or hydrochloric acid for pH adjustment, and water for injection
    Number of study animals: 42; Age: at least 6-8 weeks; Body weight range: 300-350 grams upon receipt from supplier.

Description of Experiment, Animal Allocation and Procedures:

Test Period Procedures: Animals were dosed with ARP on Day 0. On Study Day 10, all animals were euthanized, and the injection site reaction tissue/material was retrieved surgically and weighed immediately.

Figure 8A:
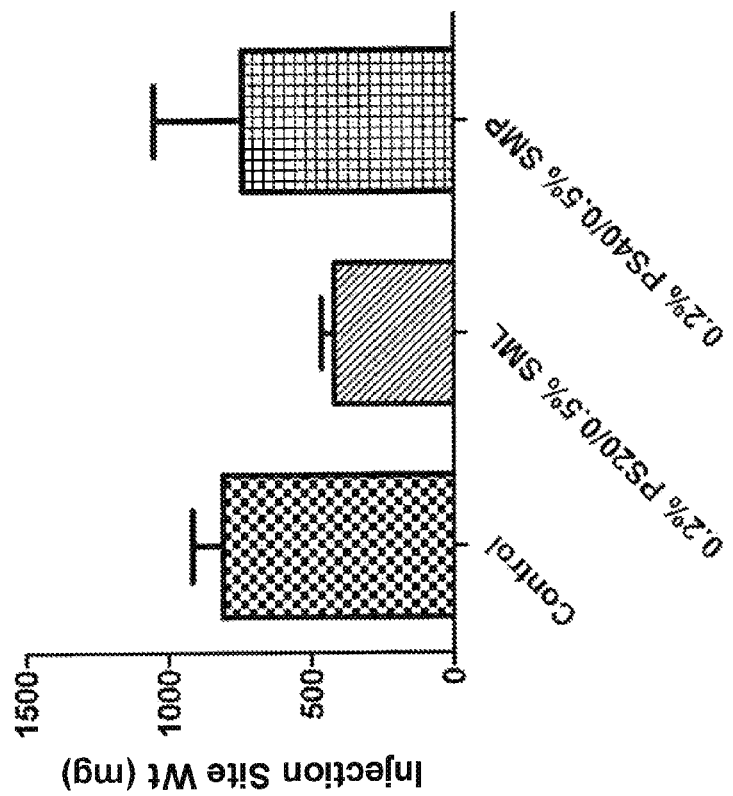

FIGS. 8A and 8B demonstrate that formulations comprising sorbitan laurate demonstrated a significant reduction in injection site reaction compared to formulations with no sorbitan laurate. FIG. 8A shows results from experiments with aripiprazole (free base), and FIG. 8B shows results from experiments with olanzapine pamoate.

EXAMPLE IV

Solubility of Compound A-7 in Vehicles Containing Varying Amounts of Sorbitan Monolaurate Sample preparation:
  a. Injection vehicles comprised of ca. 10 mM phosphate buffer, 0.2% polysorbate 20, saline and various amount of sorbitan laurate (0%-0.75%) were prepared. The injection vehicles were stirred for 4 hours before preparing suspension preparation.
  b. Approximately 1.25±0.05 g of Compound A-7 were added to 15 mL injection vehicles in a 20-mL glass scintillation vial with a ⅞"×⁵⁄₁₆" stirring bar. The suspension was vigorously stirred on Chemglass CG-1990-T-50 hotplate at 25° C. which was controlled using a thermal sensor.
  c. At each time point, a total of 3 mL of -mixed suspension were transferred into two 1.5-mL centrifuge tubes using a plastic pipette. The tubes were centrifuged at 14,000 rpm for 4 minutes. The supernatant of both tubes were combined and centrifuged again at 14,000 rpm for 4 minutes. The HPLC sample was then prepared with final (2nd) centrifuged supernatant by diluting 0.4 mL supernatant with 0.6 mL THF.
  d. Concentration of dissolved Compound A-7 was determined using HPLC.

Figure 9:
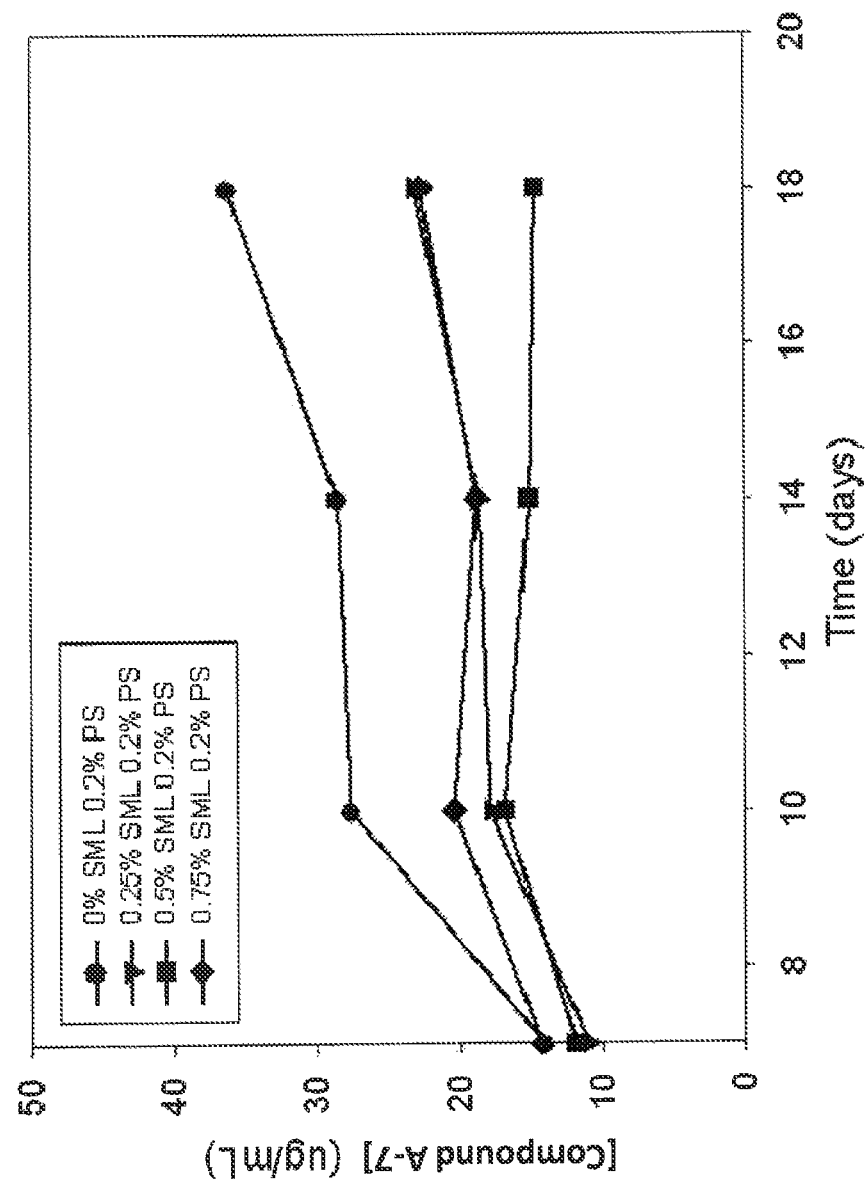

The data illustrated in FIG. 9 highlight the trends in Compound A-7 concentration in solution as a function of SML content in the injection vehicle. Surprisingly, the addition of a second surfactant, SML, decreases solubility up to 0.5 wt % SML with solubility increasing again above 0.5 wt. % (e.g. 0.75 wt %) (middle line).

EXAMPLE V

Prodrug Synthesis Procedures

Synthesis of Aripiprazole Prodrugs

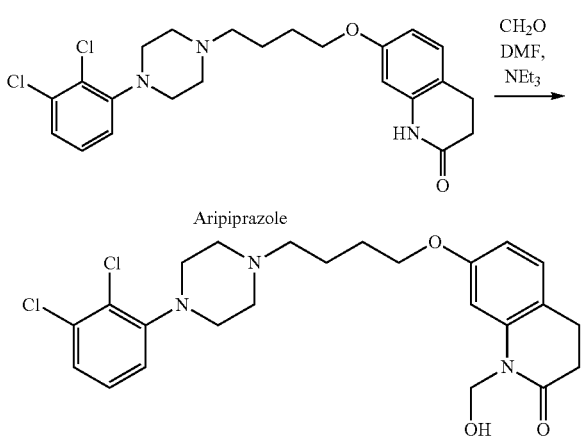

Example 1

Compound A-1: Preparation of 7-(4-(4-(2,3-dichlorophenyl)piperazin-1-yl)butoxy)-1-(hydroxymethyl)-3,4-dihydroquinolin-2(1H)-one A mixture of Aripiprazole (20 g, 45 mmol), triethylamine (1 mL, 7.1 mmol), formaldehyde (37% aqueous solution, 70 mL) and dimethylformamide (200 mL) was heated to 80° C. for 20 h. The reaction mixture was cooled, diluted with ethyl acetate (400 mL) and washed with water/brine (1:1, 3×500 mL). The organic phase was dried over MgSO$_4$, filtered and evaporated to dryness under vacuum to give hemi-aminal A-1 as a white solid (18.6 g, containing 25% Aripiprazole, 65% yield based on A-1).

Compound 1: (7-(4-(4-(2,3-dichlorophenyl)piperazin-1-yl)butoxy)-2-oxo-3,4-dihydroquinolin-1(2H)-yl)methyl acetate

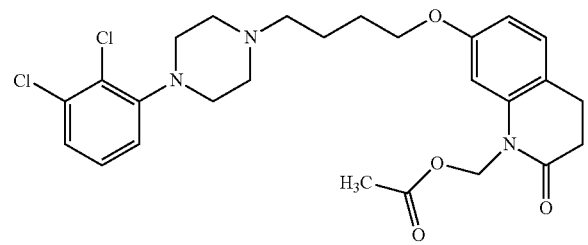 [SMILES: CC(=O)OCN1C(=O)CCc2ccc(OCCCCN3CCN(c4cccc(Cl)c4Cl)CC3)cc21]

A solution of Compound A-1 (50.63 g, 0.105 mol) in anhydrous tetrahydrofuran (THF, 80 mL) was treated with acetic anhydride (15.3 mL, 0.16 mol) and heated for 2.0 hours at 60° C. (oil-bath). To the above solution, triethylamine (2.0 mL, 0.014 mol) was added and stirred for 16 hours at 60° C. The solvent was removed using a rotator evaporator. To the resulting crude mixture, ethyl acetate (150 mL) and heptane (50 mL) was added. The solution was washed with NaHCO$_3$ (5% aqueous solution, 250 mL,). After separation of the two layers, pH of the aqueous layer was adjusted to above 7. The aqueous layer was further extracted using the organic mixture. The organic layer was separated and washed with 5% NaHCO$_3$ solution, followed by deionized water, and brine. The solution was dried using anhydrous MgSO$_4$, filtered and evaporated under vacuum. The resulting product was purified using silica gel column chromatography using ethanol: ethyl acetate (5:95) as the eluent. Fractions containing the desired product were combined and d-tartaric acid (12.5 g dissolved in 60:5 ethanol: water) was added, resulting in the precipitation of the desired product (48.78 g, 89% yield). $^1$H NMR (CDCl3, 300 MHz) δ 1.73 (m, 2H), 1.84 (m, 2H), 2.12 (s, 3H), 2.50 (t, 2H), 2.68 (m, 6H), 2.87 (dd, 2H), 3.08 (m, 4H), 3.98 (t, 2H), 5.91 (s, 2H), 6.59 (m, 2H), 6.96 (dd, 1H), 7.08 (dd, 1H), 7.15 (m, 2H).

Compound A-7: (7-(4-(4-(2,3-dichlorophenyl)piperazin-1-yl)butoxy)-2-oxo-3,4-dihydroquinolin-1(2H)-yl)methyl dodecanoate

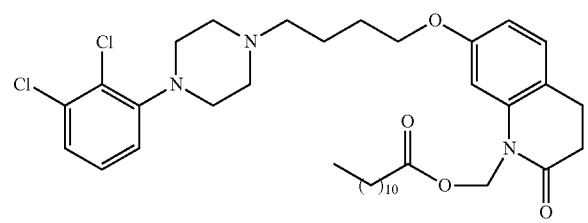

Compound A-7 was prepared in an analogous fashion to Compound 1. The desired product was isolated as a crystalline solid (0.3 g, 21% yield). The molecular weight was confirmed by mass spectrometer analysis. FIG. 2-6 shows the PXRD, IR, Raman, TGA spectrum of the desired product. $^1$H NMR (CDCl3, 300 MHz) δ 0.87 (t, 3H), 1.24 (m, 16H), 1.62 (m, 2H), 1.83 (m, 2H), 1.86 (m, 2H), 2.36 (t, 2H), 2.49 (t, 2H), 2.68 (m, 6H), 2.86 (dd, 2H), 3.08 (m, 4H), 3.97 (t, 2H), 5.91 (s, 2H), 6.59 (m, 2H), 6.96 (dd, 1H), 7.07 (dd, 1H), 7.14 (m, 2H).

Compound A-28: (7-(4-(4-(2,3-dichlorophenyl)piperazin-1-yl)butoxy)-2-oxo-3,4-dihydroquinolin-1(2H)-yl)methyl benzylcarbamate

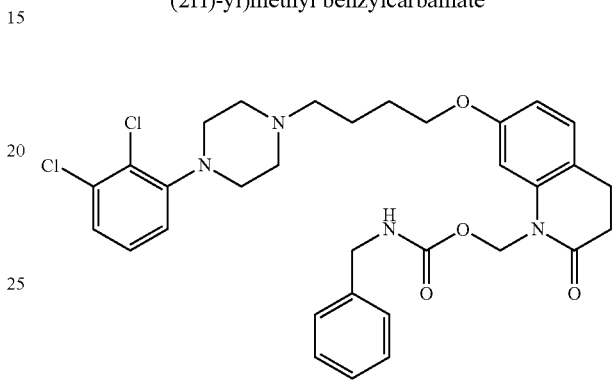

To a solution of hemi-aminal A1 (4 g, 8.4 mmol), 4-dimethylaminopyridine (0.15 g, 1.3 mmol) and triethylamine (1.1 mL, 7.5 mmol) in dichloromethane (30 mL) was added benzylisocyanate (1.03 mL, 8.3 mmol) and the reaction mixture stirred for 24 hours. The reaction mixture was then heated at 35° C. for 20 hours, cooled and washed with water/brine (1:1, 50 mL). The organic phase was dried over MgSO$_4$, filtered and evaporated under vacuum. The residue was further purified by chromatography on silica eluting with ethyl acetate/dichloromethane/methanol (1:1:0.1) to give the desired product as an off white foam (530 mg, 14% yield). $^1$H NMR (CDCl$_3$, 300 MHz) δ 1.58-1.88 (m, 4H), 2.48 (t, 2H), 2.60-2.72 (m, 6H), 2.85 (m, 2H), 300-3.12 (m, 4H), 3.96 (t, 2H), 4.40 (d, 2H), 5.13 (NH), 5.96 (s, 2H), 6.58 (dd, 1H), 6.79 (d, 1H), 6.92-6.98 (m, 1H), 7.04 (d, 1H), 7.12-7.16 (m, 1H), 7.23-7.35 (m, 6H); m/z (M$^+$H) 611.12 and 613.10.

Compound A-4: (7-(4-(4-(2,3-dichlorophenyl)piperazin-1-yl)butoxy)-2-oxo-3,4-dihydroquinolin-1(2H)-yl)methyl hexanoate

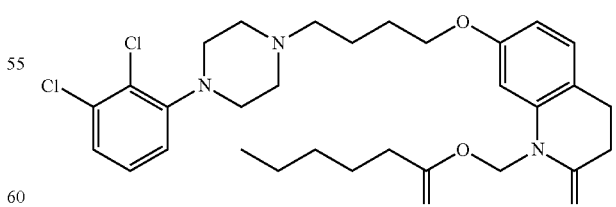

Compound A-4 was prepared in an analogous fashion to Compound A-28. The desired product was isolated as a yellow solid (3.69 g, 87% yield). $^1$H NMR (CDCl$_3$, 300 MHz) δ 0.78 (t, 3H), 1.11-1.28 (m, 4H), 1.40-1.78 (m, 6H), 2.20-2.40 (m, 4H), 2.40-2.60 (m, 6H), 2.73-2.81 (m, 2H), 2.85-3.00 (m, 4H), 3.88-4.00 (m, 2H), 5.75-5.83 (m, 2H), 6.55-6.62 (m, 2H), 7.03-7.12 (m, 2H), 7.20-7.26 (m, 2H). m/z (M+H) 576.4 and 578.4.

What is claimed is:

1. A pharmaceutical composition comprising:
(a) compound of Formula (III) or (IV):

(III)

(IV)

wherein
R³ is —CH₂OC(O)R¹, —CH₂OC(O)OR¹, —CH₂OC(O)N(R¹)₂ or —C(O)R¹;
R⁴ is —CH₂OC(O)R¹, —CH₂OC(O)OR¹, —CH₂OC(O)N(R¹)₂ or —C(O)R¹;
wherein each R¹ is independently selected from the group consisting of hydrogen, substituted or unsubstituted aliphatic, and substituted or unsubstituted aryl; and
wherein Y⁻ is a pharmaceutically acceptable counterion;
(b) sorbitan laurate;
(c) polysorbate 20; and
(d) an aqueous vehicle
wherein the composition forms an aqueous, flocculated, injectable suspension.

2. The composition of claim 1, wherein the composition comprises components (b) and (c) at a ratio that results in flocs comprising component (a), wherein the flocs settle to greater than a predetermined sediment bed height, such that components (a), (b) and (c) can be resuspended for injection.

3. The composition of claim 2, wherein the bed height is comprised of at least a 20 to 80% increase in sediment height compared to a non flocculated composition after 24 hours of undisturbed sitting.

4. The composition of claim 2, wherein components (a), (b) and (c) can be resuspended for injection within 1-60 seconds of handshaking.

5. The composition of claim 1, wherein the ratio of components (b) to (c) is such that the composition can be injected using a 20 to 25 gauge needle.

6. The composition of claim 2, wherein (a), (b), and (c) form flocs having the following sizes: Dv[10]: 2-10µm, Dv[50]: 10-30µm, and Dv[90]: less than 65µmM.

7. The composition of claim 1, wherein the ratio of components (b) to (c) is approximately 5 to 2, by weight.

8. The composition of claim 1, comprising about 0.2-1 weight percent sorbitan laurate.

9. The composition of claim 1, comprising about 0.4-0.7 weight percent sorbitan laurate.

10. The composition of claim 1, comprising about 0.5 weight percent sorbitan laurate.

11. The composition of claim 1, comprising about 0.05-0.8 weight percent polysorbate 20.

12. The composition of claim 1, comprising about 0.1-0.3 weight percent polysorbate 20.

13. The composition of claim 1, comprising about 0.2 weight percent polysorbate 20.

14. The composition of claim 1, comprising approximately 15-35 weight percent compound of formula III or IV.

15. The composition of claim 1, comprising approximately 20-30 weight percent compound of formula III or IV.

16. An injectable pharmaceutical composition comprising:
(a) a compound of formula III or IV:

(III)

(IV)

wherein
R³ is —CH₂OC(O)R¹, —CH₂OC(O)OR¹, —CH₂OC(O)N(R¹)₂ or —C(O)R¹;
R⁴ is —CH₂OC(O)R¹, —CH₂OC(O)OR¹, —CH₂OC(O)N(R¹)₂ or —C(O)R¹;
wherein each R¹ is independently selected from the group consisting of hydrogen, substituted or unsubstituted aliphatic, and substituted or unsubstituted aryl; and
wherein Y⁻ is a pharmaceutically acceptable counterion;
wherein component (a) is in a weight ratio of approximately 15-35%;
(b) sorbitan laurate in a weight ratio of approximately 0.2-1%
(c) polysorbate 20 in a weight ratio of approximately 0.05-0.8%; and
(d) an aqueous carrier.

17. An injectable composition comprising:
(a) a compound of formula III or IV:

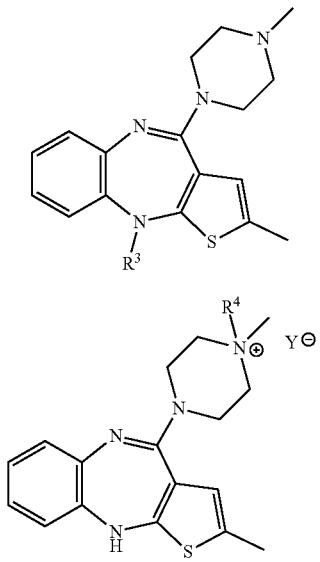

wherein
R³ is —CH₂OC(O)R¹, —CH₂OC(O)OR¹, —CH₂OC(O)N(R¹)₂ or —C(O)R¹;
R⁴ is —CH₂OC(O)R¹, —CH₂OC(O)OR¹, —CH₂OC(O)N(R¹)₂ or —C(O)R¹;
wherein each R¹ is independently selected from the group consisting of hydrogen, substituted or unsubstituted aliphatic, and substituted or unsubstituted aryl; and
wherein Y⊖ is a pharmaceutically acceptable counterion;
(b) sorbitan laurate;
(c) polysorbate 20; and
(d) an aqueous vehicle.

18. The composition of claim 17, wherein the composition is formulated for modulating tissue reaction associated with the delivery of a water-insoluble antipsychotic agent.

19. A method for treating disorders of the central nervous system, comprising administering an effective amount of the composition of claim 1 to an individual in need of such treatment.

20. The method of claim 19, wherein the disorder is selected from the group consisting of anxiety, depression, bipolar disorder, autism-related irritability, and a psychotic condition.

* * * * *